United States Patent
Park et al.

(10) Patent No.: US 10,247,824 B2
(45) Date of Patent: Apr. 2, 2019

(54) ULTRASOUND IMAGING APPARATUS AND METHOD FOR CONTROLLING THE SAME

(71) Applicant: SAMSUNG ELECTRONICS CO., LTD., Suwon-si (KR)

(72) Inventors: Sungchan Park, Suwon-si (KR); Jooyoung Kang, Yongin-si (KR); Jungho Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 860 days.

(21) Appl. No.: 14/683,304

(22) Filed: Apr. 10, 2015

(65) Prior Publication Data
US 2015/0289847 A1 Oct. 15, 2015

(30) Foreign Application Priority Data
Apr. 15, 2014 (KR) ........................ 10-2014-0044637

(51) Int. Cl.
*A61B 8/00* (2006.01)
*A61B 8/08* (2006.01)
(Continued)

(52) U.S. Cl.
CPC ...... *G01S 15/8977* (2013.01); *G01S 7/52077* (2013.01); *G01S 15/8915* (2013.01);
(Continued)

(58) Field of Classification Search
CPC ............. G01S 15/8977; G01S 7/52077; G01S 15/8915; G10K 11/346
See application file for complete search history.

(56) References Cited

U.S. PATENT DOCUMENTS

2002/0049379 A1   4/2002   Adam et al.
2005/0057392 A1   3/2005   Blunt et al.
(Continued)

FOREIGN PATENT DOCUMENTS

JP   5000030 B1   8/2012
KR   10-0311482 B1   10/2001
(Continued)

OTHER PUBLICATIONS

O'Haver, "Resolution enhancement (Peak Sharpening)" (archived Mar. 29, 2013 at https://web.archive.org/web/20130329175929/https://terpconnect.umd.edu/~toh/spectrum/ResolutionEnhancement.html).*

*Primary Examiner* — Thomas J Hong
*Assistant Examiner* — Colin T. Sakamoto
(74) *Attorney, Agent, or Firm* — Sughrue Mion, PLLC

(57) ABSTRACT

The present disclosure provides an ultrasound imaging apparatus. The ultrasound imaging apparatus includes an ultrasonic probe for transmitting an ultrasound signal toward an object, receiving an echo ultrasound signal reflected from the object, and transforming the echo ultrasound signal to an electric signal; a beamformer for beamforming and outputting the electric signal; an image reconstruction unit for generating a reconstructed image by applying a Point Spread Function (PSF) to an ultrasonic image corresponding to the output signal; and an image post-processor for performing filtering to emphasize a peak point of the reconstructed image. The use of a filter to emphasize a peak point may facilitate an accurate setting of a phase parameter to be used in estimation of a PSF. Accordingly, an almost ideal PSF may be estimated, image reconstruction is performed using the estimated PSF, and thus a high resolution image may be obtained.

17 Claims, 25 Drawing Sheets

(51) Int. Cl.
*G01S 7/52* (2006.01)
*G01S 15/89* (2006.01)
*G10K 11/34* (2006.01)

(52) U.S. Cl.
CPC .......... *G10K 11/346* (2013.01); *A61B 8/5207* (2013.01); *A61B 8/54* (2013.01)

(56) References Cited

U.S. PATENT DOCUMENTS

| | | | | |
|---|---|---|---|---|
| 2007/0296833 | A1* | 12/2007 | Corcoran | H04N 5/23248 348/231.99 |
| 2009/0013020 | A1* | 1/2009 | Eguchi | G06T 5/003 708/270 |
| 2013/0010138 | A1* | 1/2013 | Bigioi | G06K 9/00261 348/208.2 |
| 2013/0090559 | A1* | 4/2013 | Park | A61B 8/5207 600/443 |
| 2014/0153793 | A1* | 6/2014 | Goharrizi | G06T 5/004 382/128 |

FOREIGN PATENT DOCUMENTS

| KR | 10-2007-0085364 A | 8/2007 |
|---|---|---|
| KR | 10-2013-0037112 A | 4/2013 |

\* cited by examiner

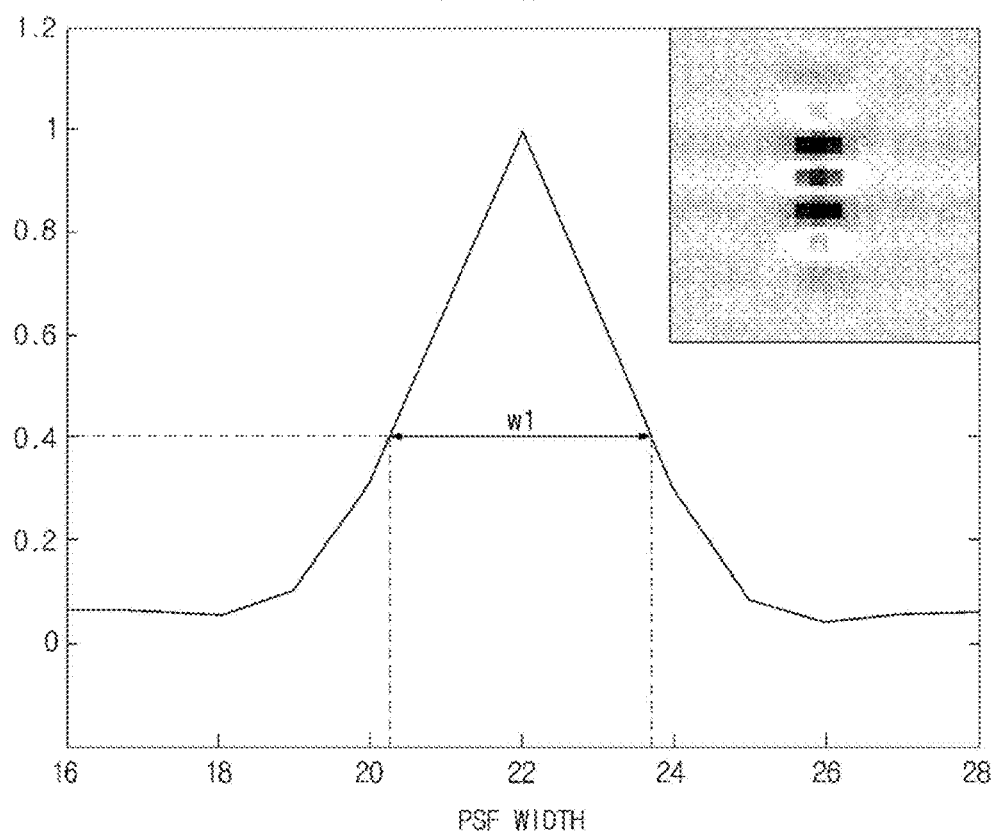

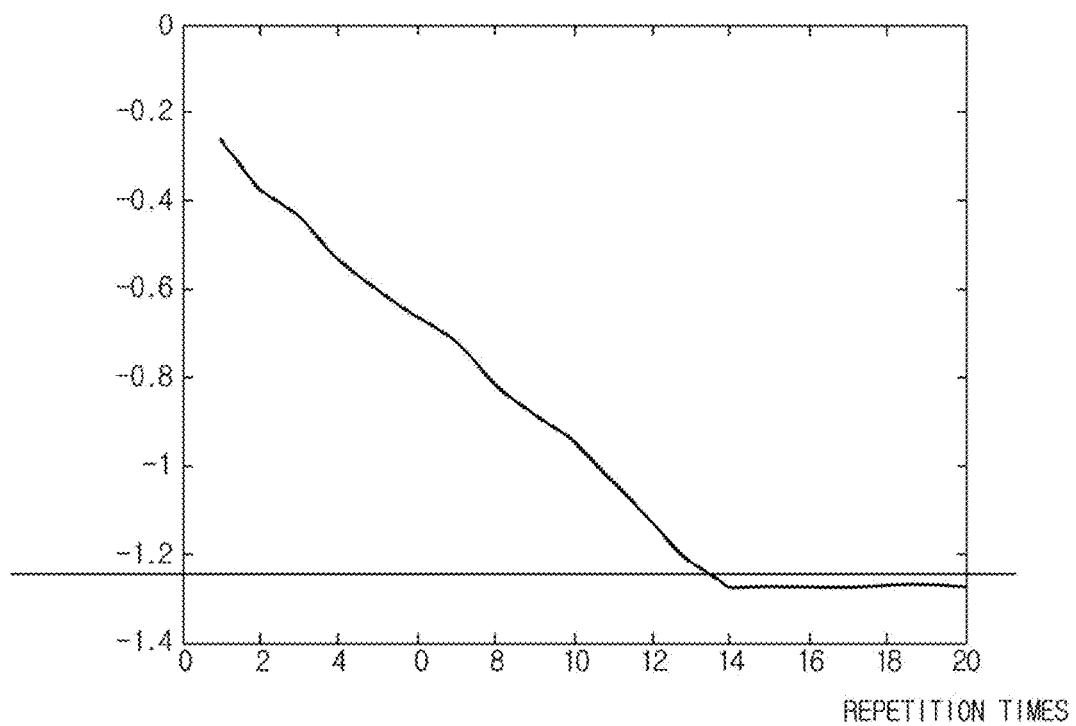

FIG. 14A
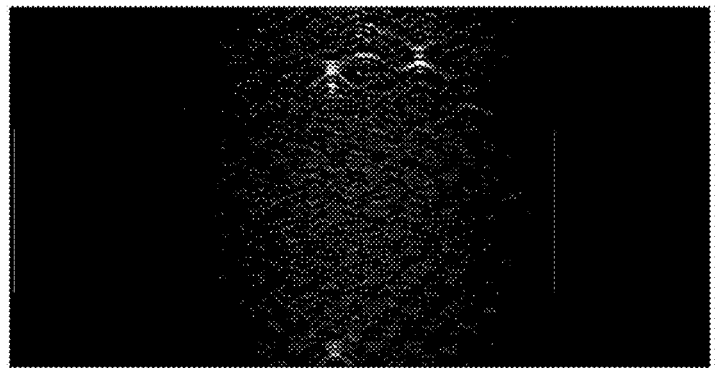
(a) FIRST PSF
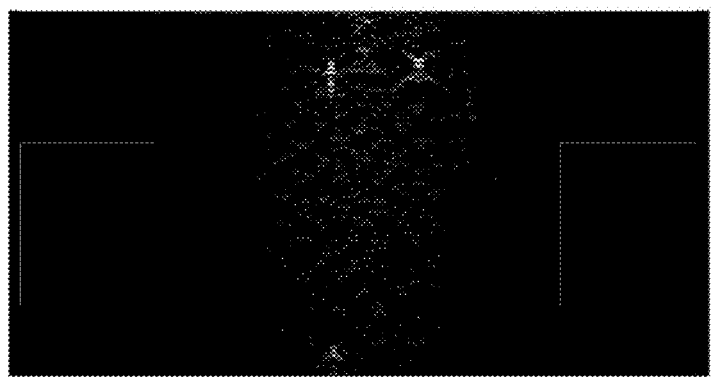
(b) FIRST RECONSTRUCTED IMAGE
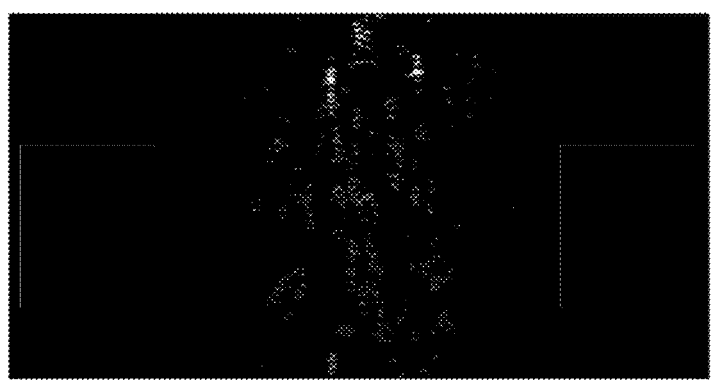
(c) FIRST FILTERED IMAGE

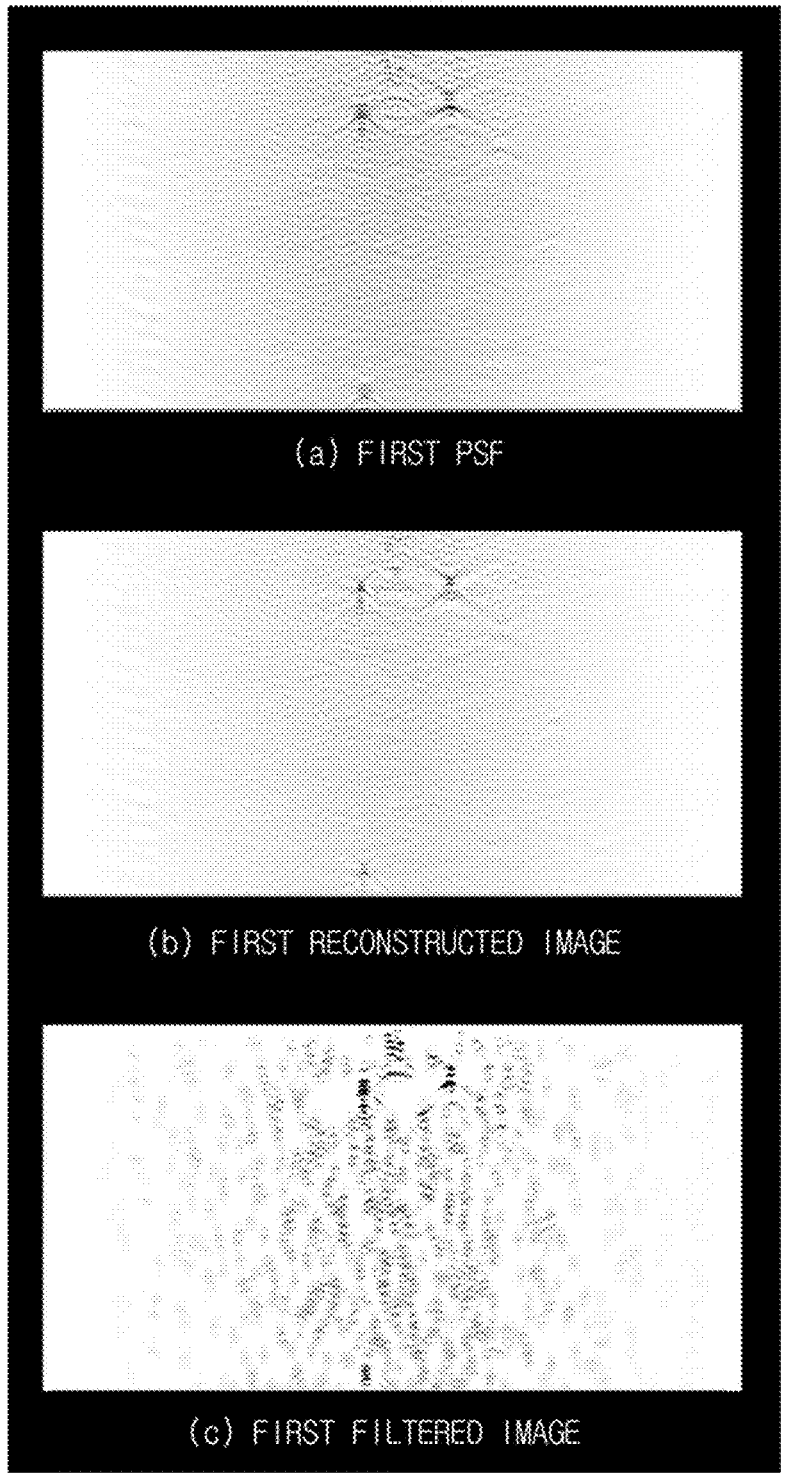

FIG. 15A
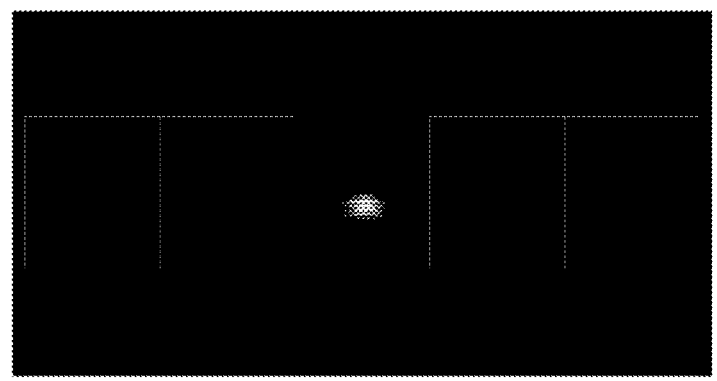
(a) FINAL PSF
(b) FINAL RECONSTRUCTED IMAGE

ULTRASOUND IMAGING APPARATUS AND METHOD FOR CONTROLLING THE SAME

CROSS-REFERENCE TO RELATED APPLICATION(S)

This application claims priority under 35 U.S.C. § 119(a) from a Korean patent application filed on Apr. 15, 2014 in the Korean Intellectual Property Office and assigned Serial No. 10-2014-0044637, the disclosure of which is incorporated herein by reference in its entirety.

TECHNICAL FIELD

The present disclosure relates to an ultrasound imaging apparatus and a method for controlling the same, which performs reconstruction and filtering on an ultrasonic image.

BACKGROUND

An ultrasound imaging apparatus irradiates ultrasound signals toward an object through the surface of the object, detects ultrasound signals reflected from the object, i.e., echo ultrasound signals, and then provides necessary information about an examined part inside the object, such as a tomogram of a soft tissue or bloodstream, by generating an image about the examined part.

The ultrasound imaging apparatus is widely used for medical examination at maternity, cardiology, abdomen, and urology clinics, because it is compact and inexpensive and has noninvasive and non-destructive properties as compared with another type of diagnostic imaging apparatus, e.g., X-ray device, Computerized Tomography (CT) scanner, Magnetic Resonance Image (MRI), and diagnostic nuclear medical apparatuses.

The ultrasound imaging apparatus uses a probe, which is a means for generating ultrasound signals, in order to obtain an ultrasonic image of the object. The probe includes at least one transducer, each transmitting an ultrasound signal toward the object and receiving an echo ultrasound signal from the object. In this regard, beamforming is performed to deal with time differences among echo ultrasound signals received by the transducers. The ultrasound imaging apparatus obtains an ultrasonic image of the object based on the beamformed signals.

SUMMARY

Exemplary embodiments provide an ultrasound imaging apparatus and method for controlling the same, which performs reconstruction of an ultrasonic image by means of a filter to stress a peak point.

In accordance with an aspect of one or more exemplary embodiments, an ultrasound imaging apparatus is provided. The ultrasound imaging apparatus includes an ultrasonic probe configured for transmitting an ultrasound signal toward an object, receiving an echo ultrasound signal which is reflected from the object, and transforming the received echo ultrasound signal to an electric signal; a beamformer configured for beamforming and outputting the electric signal; an image reconstructor configured for generating a reconstructed image by applying a Point Spread Function (PSF) to an ultrasonic image which corresponds to the output signal; and an image post-processor configured for performing filtering in order to emphasize a peak point of the reconstructed image.

The image post-processor may be further configured to detect a peak point from the reconstructed image, to generate a peak sharpening filter based on the detected peak point, and to perform filtering on the reconstructed image by using the peak sharpening filter.

The image post-processor may be further configured to generate an impulse signal for the peak point, and to use the peak point to generate the peak sharpening filter in a Gaussian form.

The image reconstructor may be further configured to set a parameter; to estimate a PSF by using the parameter; to apply the estimated PSF to the ultrasonic image; and to generate a reconstructed image based on the ultrasonic image.

The image reconstructor may be further configured to update the parameter by using the filtered image.

The image reconstructor may be further configured to estimate an updated PSF by using the updated parameter.

The image reconstructor may be further configured to generate an updated reconstructed image by applying the updated PSF to the ultrasonic image.

The image reconstructor may be further configured to transform the ultrasonic image into the Cepstrum domain; and to estimate a PSF by using a Cepstrum method for estimating a two dimensional (2D) PSF in the Cepstrum domain.

The image reconstructor may be further configured to generate the reconstructed image by performing a deconvolution of the ultrasonic image and the PSF.

The ultrasound imaging apparatus may further include an image divider configured for dividing the ultrasonic image into at least one area.

The image reconstructor may be further configured to generate at least one reconstructed image for each of the at least one area.

The image post-processor may be further configured to perform filtering on each of the at least one reconstructed image.

The ultrasound imaging apparatus may further include an image composer configured for composing the at least one reconstructed image.

In accordance with another aspect of one or more exemplary embodiments, a method for controlling an ultrasound imaging apparatus is provided. The method includes transmitting an ultrasound signal toward an object, receiving an echo ultrasound signal reflected from the object, and transforming the received echo ultrasound signal to an electric signal; beamforming and outputting the electric signal; generating a reconstructed image by applying a Point Spread Function (PSF) to an ultrasonic image which corresponds to the output signal; and performing filtering in order to emphasize a peak point of the reconstructed image.

The performing filtering may include detecting the peak point from the reconstructed image, generating a peak sharpening filter based on the detected peak point, and performing filtering on the reconstructed image by using the peak sharpening filter.

The performing filtering may include generating an impulse signal for the peak point, and using the peak point to generate a peak sharpening filter in a Gaussian form.

The generating the reconstructed image may include setting a parameter; estimating a PSF by using the parameter; applying the estimated PSF to the ultrasonic image; and generating a reconstructed image based on the ultrasonic image.

The setting a parameter may include updating the parameter by using the filtered image.

The estimating a PSF may include estimating an updated PSF by using the updated parameter.

The generating a reconstructed image may include generating an updated reconstructed image by applying the estimated updated PSF to the ultrasonic image.

Estimating a PSF may include transforming the ultrasonic image into the Cepstrum domain; and estimating a PSF by using a Cepstrum method for estimating a two dimensional (2D) PSF in the Cepstrum domain.

The generating a reconstructed image may include generating the reconstructed image by performing a deconvolution of the ultrasonic image and the PSF.

Other aspects, advantages, and salient features of the exemplary embodiments will become apparent to those skilled in the art from the following detailed description, which, taken in conjunction with the annexed drawings, discloses exemplary embodiments of the present disclosure.

BRIEF DESCRIPTION OF THE DRAWINGS

The above and other features and advantages of the present disclosure will become more apparent by describing in detail exemplary embodiments thereof with reference to the attached drawings in which:

FIGS. 10A, 10B, and 10C illustrate Point Spread Functions (PSFs) which respectively correspond to divided areas of FIG. 9A;

FIG. 13 is a graph of a phase parameter as a function of repetition times;

FIG. 14A illustrates an initially estimated PSF, a first reconstructed image, and an image obtained by filtering the first reconstructed image, and FIG. 14B illustrates color inversion image of FIG. 14A;

FIG. 15A illustrates a finally estimated PSF and a finally reconstructed image.

Throughout the drawings, like reference numerals will be understood to refer to like parts, components, and structures.

DETAILED DESCRIPTION

Figure 1:
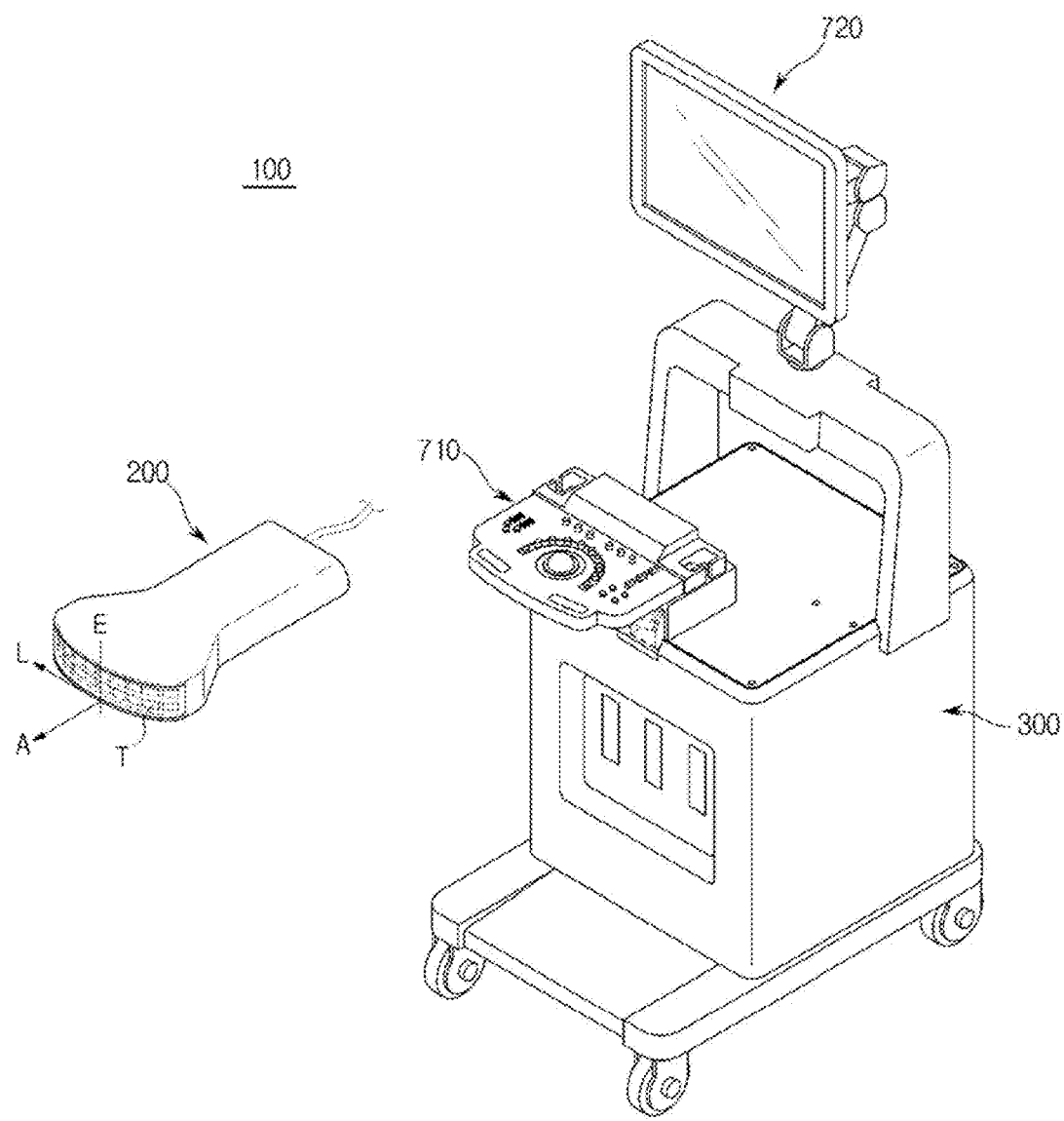
FIG. 1 is a perspective view of an ultrasound imaging apparatus, according to an exemplary embodiment.

Exemplary embodiments will now be described more fully with reference to the accompanying drawings, in which exemplary embodiments of the disclosure are shown. The exemplary embodiments may, however, be embodied in many different forms and should not be construed as being limited to the exemplary embodiments set forth herein; rather, these exemplary embodiments are provided so that this disclosure will be thorough and complete, and will fully convey the concept of the present disclosure to those skilled in the art. Like reference numerals in the drawings denote like elements, and thus their description will be omitted. In the description of the exemplary embodiments, if it is determined that a detailed description of commonly-used technologies or structures related to the exemplary embodiments may unnecessarily obscure the subject matter of the exemplary embodiments, the detailed description will be omitted. It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Further, as used herein, the term "unit" may refer to an element or component which is implemented in hardware, i.e., as a hardware device and/or as circuitry, or to an element or component which is implemented in software.

Exemplary embodiments will now be described with reference to accompanying drawings.

FIG. 1 is a perspective view of an ultrasound imaging apparatus, according to an exemplary embodiment.

As shown in FIG. 1, an ultrasound imaging apparatus 100 may include a probe 200, a main unit 300, an input unit (also referred to herein as an "input device") 710, and a display unit (also referred to herein as a "display device" and/or as a "display") 720.

The probe 200 is connected to an end of a cable, the other end of which may be connected to a male connector (not shown). The mail connector may be physically coupled with a female connector (not shown) of the main unit 300.

The probe 200 may include at least one transducer T, and may use each of the at least one transducer T to transmit ultrasound signals toward an object and receive echo ultrasound signals reflected from the object. The at least one transducer T may forms at least one row at one end of the probe 200, as shown in FIG. 1.

The object may include, but not exclusively, any one or more of a living body of a human or animal, an organ in the living body, such as blood vessels, bones, muscles, etc., and/or anything whose internal structure may be imaged by the ultrasound imaging apparatus 100.

Three directions which are mutually perpendicular to one another with respect to a central point of the transducer may be defined as axis direction A, lateral direction L, and elevation direction E. Specifically, the axis direction A corresponds to a direction in which an ultrasound signal is irradiated; the lateral direction L corresponds to a direction in which the transducers are arranged, i.e., a direction of a row of the transducers; and the elevation direction E corresponds to a direction which is perpendicular to each of the axis direction A and the lateral direction L.

Figure 3:
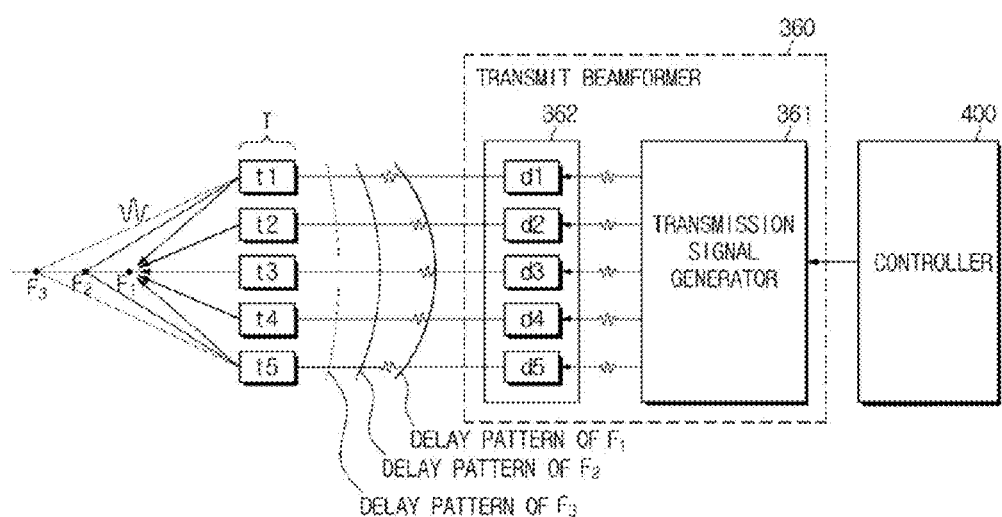
FIG. 3 is a block diagram of a transmit beamformer.

The main unit 300 may contain main components of the ultrasound imaging apparatus 100, e.g., a transmission signal generator (361 of FIG. 3). When an examiner inputs an ultrasound diagnosis command, the transmission signal generator 361 may generate and transmit a transmission signal to the probe 200.

There may be one or more female connectors in the main unit 300, which are physically coupled with male connectors connected to cables, thereby facilitating a communication of signals between the main unit 300 and the probe 200. For example, a transmission signal generated by the transmission signal generator 361 may be sent to the probe 200 via a male connector which is coupled with the female connector of the main unit 300 and via the cable.

In addition, a plurality of casters may be mounted on the bottom of the main unit 300 in order to fix the ultrasound imaging apparatus 100 in a particular place and/or in order to facilitate a movement of the ultrasound imaging apparatus 100 in a particular direction.

The input unit 710 may receive, from the user, a command which relates to an operation of the ultrasound imaging apparatus 100. For example, the user may input a command which relates to any one or more of starting an ultrasonic examination, selecting a part to be examined, selecting an examination type, selecting a mode for an output ultrasonic image, etc., via the input unit 710. The command input via the input unit 710 may be sent to the main unit 300 via wired and/or wireless communications.

The term 'user' as used herein may refer to a medical personnel who performs diagnosis with the ultrasound imaging apparatus 100, including any one or more of a doctor, a radiographer, a nurse, etc., but is not limited thereto and thus may refer to anyone who uses the ultrasound imaging apparatus 100. As an example of the mode for the ultrasonic image, there may be any one or more of an Amplitude mode (A mode), a Brightness mode (B mode), a Doppler mode (D mode), an Elastography mode (E mode), a Motion mode (M mode), etc.

The input unit 710 may, but not exclusively, include at least one of a keyboard, a mouse, a trackball, a touch screen, a foot switch, and a foot pedal.

The input unit 710 may be located on the top of the main unit 300 as shown in FIG. 1, or may be contained in a lower part of the main unit 300 if it is implemented with a foot switch or foot pedal.

If the input unit 710 is implemented in a Graphical User Interface (GUI), such as, for example, in a touch screen, the input unit 710 may be displayed on the display unit 720, which will be described below.

There may be one or more probe holders which are positioned within relatively close proximity to the input unit 710 to hold the probe 200. Accordingly, the user may keep the probe 200 in the probe holder while the ultrasound imaging apparatus 100 is not used.

The display unit 720 displays an image obtained during an ultrasonic diagnostic process. The display unit 720 displays the image according to a mode selected by the user. If no mode is selected, the image may be displayed in a default mode set by the user in advance, e.g., B mode.

The display unit 720 may be installed in combination with the main unit 300, or separately from the main unit 300. Although not shown in FIG. 1, a separate sub-display unit may be included in the ultrasound imaging apparatus 100 in order to display applications related to operations of the ultrasound imaging apparatus 100 (e.g., menus or guides required for ultrasonic diagnosis).

The display unit 720 may include any one or more of a Cathode Ray Tube (CRT), a Liquid Crystal Display (LCD), Organic Light Emitting Diodes (OLEDs), etc., but is not limited thereto.

Figure 2:
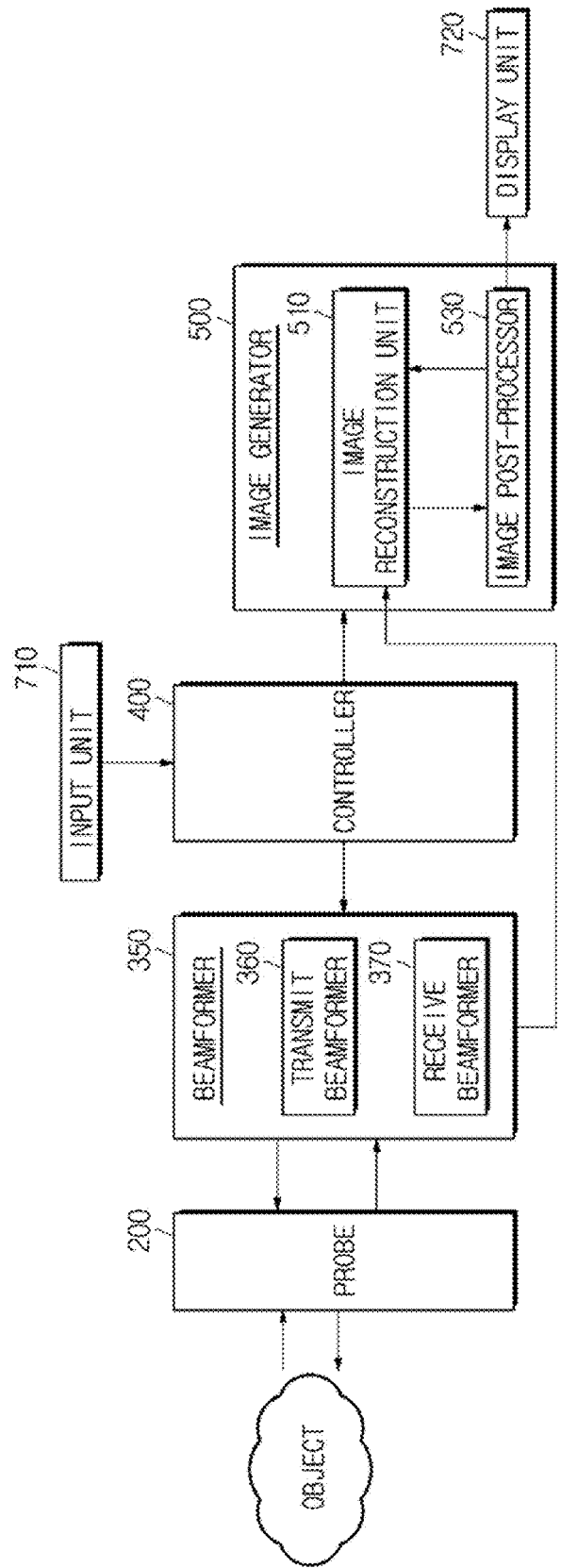
FIG. 2 is a control block diagram of an ultrasound imaging apparatus, according to an exemplary embodiment.

FIG. 2 is a control block diagram of an ultrasound imaging apparatus, according to an exemplary embodiment.

Referring to FIG. 2, the ultrasound imaging apparatus 100 may image an inside of an object by means of the probe 200, a beamformer 350, a controller 400, an image generator 500, the input unit 710, and the display unit 720.

The controller 400 may control general operations of the ultrasound imaging apparatus 100. Specifically, the controller 400 may generate control signals to control at least one of a transmit beamformer 360, a receive beamformer 370, the image generator 500, and the display unit 720 in response to an instruction or command input via the input unit 710. Sometimes, the controller 400 may generate control signals to control corresponding components in response to an instruction or command received from an external device via wired and/or wireless communication.

The probe 200 includes at least one transducer T to transmit ultrasound signals to an object, receive echo ultrasound signals reflected from the object, and perform transformation between electric signals and ultrasound signals.

Specifically, when the probe 200 is supplied with power from an external power supply or an internal electricity storage device, e.g., a battery, the transducers generate ultrasound signals while vibrating due to the applied current and irradiate the ultrasound signals toward an external object. Each transducer receives an echo ultrasound signal reflected and returned from the object, and generates a current while vibrating due to the received echo ultrasound signal, the current having a frequency which corresponds to the vibration frequency.

The transducer T may include any one or more of a Magnetostrictive Ultrasound Transducer (MUT) that uses magnetostrictive effects of a magnetic substance, a Capacitive Micromachined Ultrasonic Transducer (cMUT) that uses vibration of hundreds or thousands of microfabricated thin films, and/or a Piezoelectric Ultrasonic Transducer (PUT) that uses piezoelectric effects of a piezoelectric material or substance.

The transducers T may include any one or more of a linear array, a convex array, a phased array, and/or a sector array of transducers, etc., which may be arranged in a form of a row or a matrix. If the transducers T are arranged in a row, they may be swung in the elevation direction to obtain multiple ultrasonic images; and if they are arranged in a form of a matrix, multiple ultrasonic images may be obtained by using only a single transmission of ultrasound signals.

However, the transducers are not limited thereto, but may be implemented with any other types of transducers known to persons of ordinary skill in the art.

The beamformer 350 includes a transmit beamformer 360 and a receive beamformer 370, which are respectively configured to perform transformation between analog and digital signals and to adjust time differences of ultrasound signals transmitted by or received from the at least one transducers T.

Figure 4:
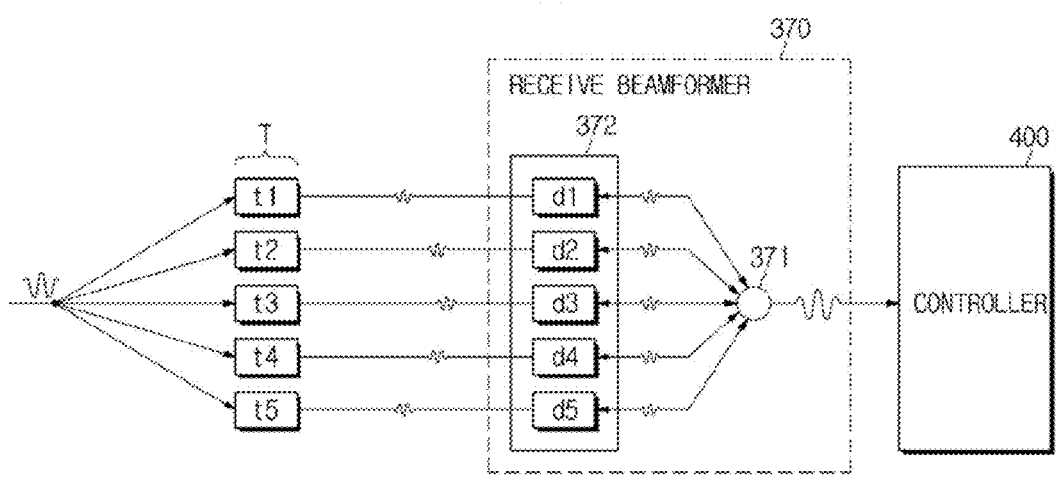
FIG. 4 is a block diagram of a receive beamformer.

Configurations and operations of the beamformer 350 will now be described with reference to FIGS. 3 and 4. FIGS. 3 and 4 are block diagrams of the transmit beamformer 360 and receive beamformer 370, respectively.

Referring to FIG. 3, the transmit beamformer 360 may use transmission signal generator 361 and time delayer 362 to perform transmit beamforming. Transmit beamforming refers to focusing ultrasound signals generated by at least one transducers T on a focal point. In this aspect, transmit beamforming refers to controlling the transducers T to generate ultrasound signals in a predetermined order, in order to deal with arrival time differences of the ultrasound signals at the focal point.

More specifically, the signal generator 361 of the transmit beamformer 360 generates a transmission signal for at least one transducer T in response to a control signal of the controller 400. In this regard, the transmission signal may be generated in a high frequency alternating current (AC) in accordance with the number of the transducers. The transmission signal generated by the transmit signal generator 361 is sent to the time delayer 362.

The time delayer 362 may adjust a time for the transmission signal to arrive at the transducer T by delaying the transmission signal. When the transmission signal with the time delayed by the time delayer 362 is applied to the transducer T, the transducer T generates an ultrasound signal which corresponds to the frequency of the transmit signal. An ultrasound signal generated by each transducer T is focused on the focal point. The position of the focal point where the ultrasound generated by the transducer T is focused may depend on which type of delay pattern is applied to the transmit signal.

In the example illustrated in FIG. 3, five transducers t1, t2, t3, t4, and t5 are illustrated and three types of delay pattern to be applied to transmission signals are illustrated with thick, medium, and thin solid lines.

If a delay pattern having a type of the thick solid line is applied to the transmission signals generated by the transmission signal generator 361, corresponding ultrasound signals generated by transducers t1 to t5 are focused on a first focal point F1.

If a delay pattern having a type of the medium solid line is applied to the transmission signals generated by the transmission signal generator 361, corresponding ultrasound signals generated by transducers t1 to t5 are focused on a second focal point F2, which is farther than the first focal point F1.

If a delay pattern having a type of the thin solid line is applied to the transmission signals generated by the transmission signal generator 361, corresponding ultrasound signals generated by transducers t1 to t5 are focused on a third focal point F3, which is farther than the second focal point F2.

As described above, the location of the focal point depends on the delay pattern applied to the transmission signal generated by the transmission signal generator 361. While if only one delay pattern is applied, ultrasound signals to be irradiated toward an object are focused on a fixed point (fixed focusing), if different delay patterns are applied, ultrasound signals to be irradiated toward the object are focused on multiple focal points (multi-focusing).

As such, ultrasound signals generated by multiple transducers T are fixedly focused on a single point or multi-focused on multiple points, the focused ultrasound signals being irradiated toward the inside of the object. The ultrasound signals irradiated toward the inside of the object are reflected from a target part within the object as echo ultrasound signals, and the echo ultrasound signals are received by the transducers T. The transducers T transform the echo ultrasound signals to electrical signals for output. The transformed electrical signals herein may be defined as received signals S. The received signals S output from the transducers T are amplified, filtered, converted into digital signals, and then provided to the receive beamformer 370.

Referring to FIG. 4, the receive beamformer 370 may include a time difference compensator 372 and a focusing unit (also referred to herein as a "focuser") 371, which are configured to perform receive beamforming on the received signals S which have been converted into digital signals. Receive beamforming refers to focusing the received signals S output from the transducers T after time differences among the received signals S are compensated.

Specifically, the time difference compensator 372 enables the received signals S output from the transducers T to be received by the focusing unit 371 at the same time by delaying each of the received signals S by a respective predetermined amount of time.

The focusing unit 371 may focus the received signals S with time difference compensated by the time difference compensator 372 into a single signal. The focusing unit 371 may focus the received signals S by applying a respective predetermined weight, e.g., a beamforming coefficient, to each received signal in order to stress (i.e., emphasize or accentuate) or attenuate the received signal S relative to the other received signals. The focused received signals S are provided to the image generator 500, and the signal provided to the image generator 500 may be defined as an input signal I.

Referring again to FIG. 2, the image generator 500 may include an image reconstruction unit (also referred to herein as an "image reconstructor") 510 and an image post-processor 530.

The image generator 500 obtains a reconstructed image which is similar to an original image of the target part by estimating an appropriate Point Spread Function (PSF) and performing a deconvolution operation based on the estimated PSF. Original and reconstructed images will be described in more detail in connection with FIGS. 5A, 5B, 6A, and 6B.

Figure 5A:
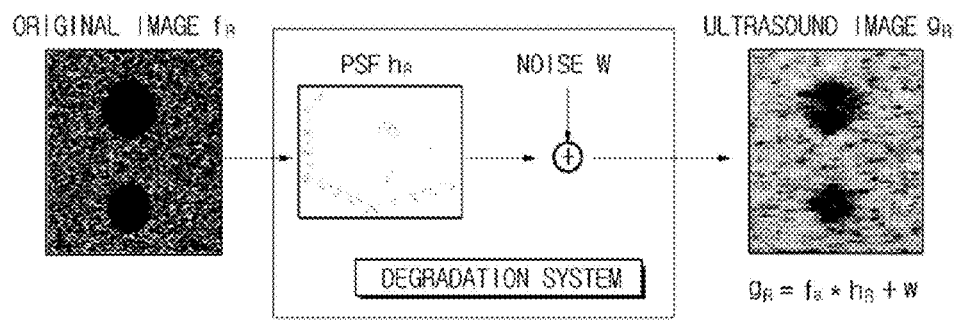
FIG. 5A illustrates a relationship between an original image and an ultrasonic image of a target part of an object.
Figure 5B:
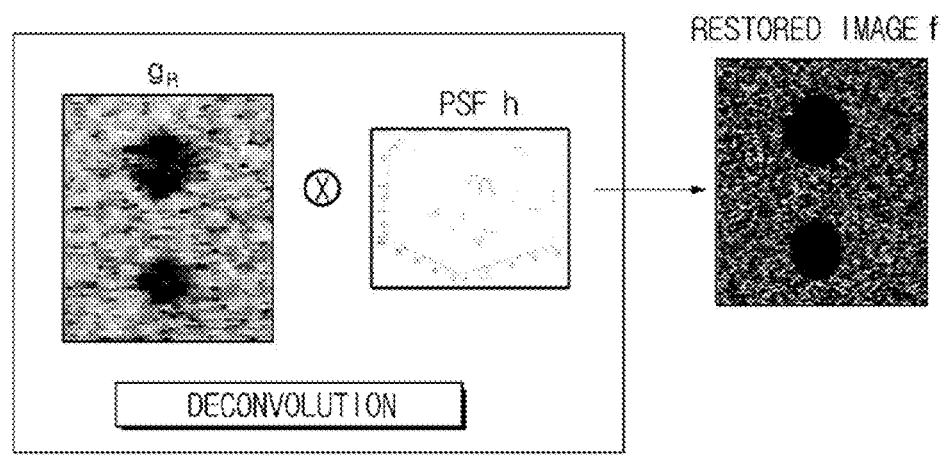
FIG. 5B illustrates a relationship between an ultrasonic image and a reconstructed image of a target part.

FIG. 5A illustrates a relationship between an original image and an ultrasonic image of a target part of an object; and FIG. 5B illustrates a relationship between an ultrasonic image and a reconstructed image of a target part.

Referring to FIG. 5A, an original image $f_R$ and an ultrasonic image $g_R$ are illustrated on the left side and the right side of the figure, respectively. Referring to FIG. 5B, an ultrasonic image $g_R$ and a reconstructed image f are illustrated on the left side and the right side of the figure, respectively. The original image $f_R$ refers to an ideal image with respect to a target part of an object, and the ultrasonic image $g_R$ refers to an image which is generated based on the aforementioned input signal I. The reconstructed image f refers to an image which results from reconstruction of the ultrasonic image $g_R$ to be as similar to the original image $f_R$ as possible.

The input signal I is provided after undergoing transmission and reception of ultrasound signals in the probe 200 and beamforming in the beamformer 350. In particular, the input signal I is a signal modified due to technical or mechanical properties of the probe 200 or beamformer 350 and to which noise has been further added. Thus, as shown in FIG. 5A, the ultrasonic image $g_R$ generated based on the input signal I has a degraded quality with blurred edges and noise included, as compared to the original image $f_R$. A relationship between the original image and the ultrasonic image will be described in more detail with reference to FIGS. 6A and 6B.

Figure 6A:
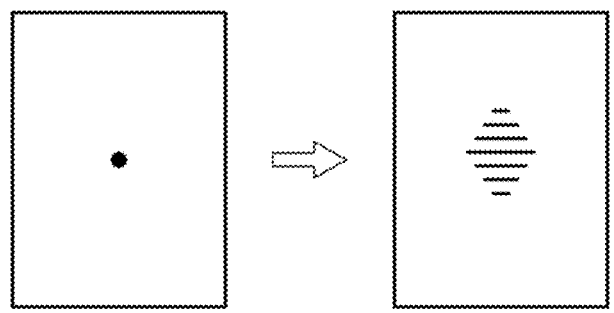
FIG. 6A illustrates an original image and an ultrasonic image of a target part.

FIG. 6A illustrates an original image and an ultrasonic image of a target part on the left side and the right side of the figure, respectively. As shown in FIG. 6A, when a target part is represented as a clear dot in an original image, the target part in the ultrasonic image is represented as being spread in all directions. Such a difference between the original image and the ultrasonic image grows as a depth to the target part becomes deeper. A direction in which the depth becomes deeper may be defined as an increased direction of axial direction.

Figure 6B:
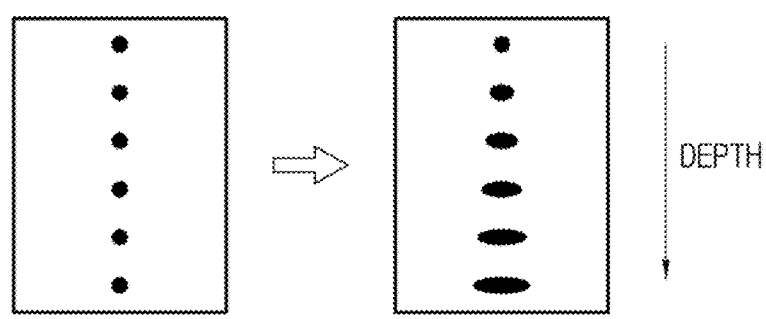
FIG. 6B illustrates an original image and an ultrasonic image of target parts having different depths.

FIG. 6B illustrates an original image and an ultrasonic image of target parts having different depths on the left side and the right side of the figure, respectively. As shown in FIG. 6B, a target part located relatively near the probe 200 is represented in a shape similar to the target part of an original image, as illustrated at the top portion of the ultrasonic image. Conversely, it is seen that a target part located relatively far from the probe 200 is represented in a quite different shape from the target part of the original image, as illustrated at the bottom portion of the ultrasonic image.

As described above, the ultrasonic image $g_R$ is generated with degraded quality due to technical or mechanical properties of the probe 200 or beamformer 350 and the noise. In this regard, given that modifications due to the technical or mechanical properties of the probe 200 or beamformer 350 are represented by a PSF $h_R$ and the noise is represented by w, the relationship between the original image $f_R$ and the ultrasound image $g_R$ may be represented in the spatial domain as expressed in the following equation 1:

$$g_R(m,n)=f_R(m,n)*h_R(m,n)+w(m,n) \quad (1)$$

where $f_R$ indicates an original image, $g_R$ indicates an ultrasonic image, $h_R$ indicates a PSF, w indicates noise, and operation * refers to convolution.

Assuming that there is no noise, the ultrasonic image $g_R$ may be represented by a result of a convolution operation of the original image $f_R$ and the PSF $h_R$. Thus, once the PSF $h_R$ is known, an original image $f_R$ corresponding to an ultrasonic image $g_R$ may be obtained by performing a deconvolution operation of the ultrasonic image $g_R$ and the PSF $h_R$.

Hence, as shown in FIG. 5B, the image generator 500 may obtain a reconstructed image f identical or similar to the original image $f_R$ of the target part by estimating an appropriate PSF h and performing deconvolution of the estimated PSF h and the ultrasonic image g.

Specifically, the image reconstruction unit 510 estimates the PSF based on the ultrasonic image. Then, the image reconstruction unit 510 obtains a reconstructed image for the ultrasonic image by performing deconvolution with the estimated PSF. The image post-processor 530 performs filtering on the reconstructed image. Then, the image reconstruction unit 510 estimates an updated PSF based on the filtered image and performs deconvolution with the newly updated PSF. Repetition of the procedure enables a more accurate estimation of the PSF and facilitates to obtain a final reconstructed image that is identical or more similar to the original image of the target part.

Figure 7:
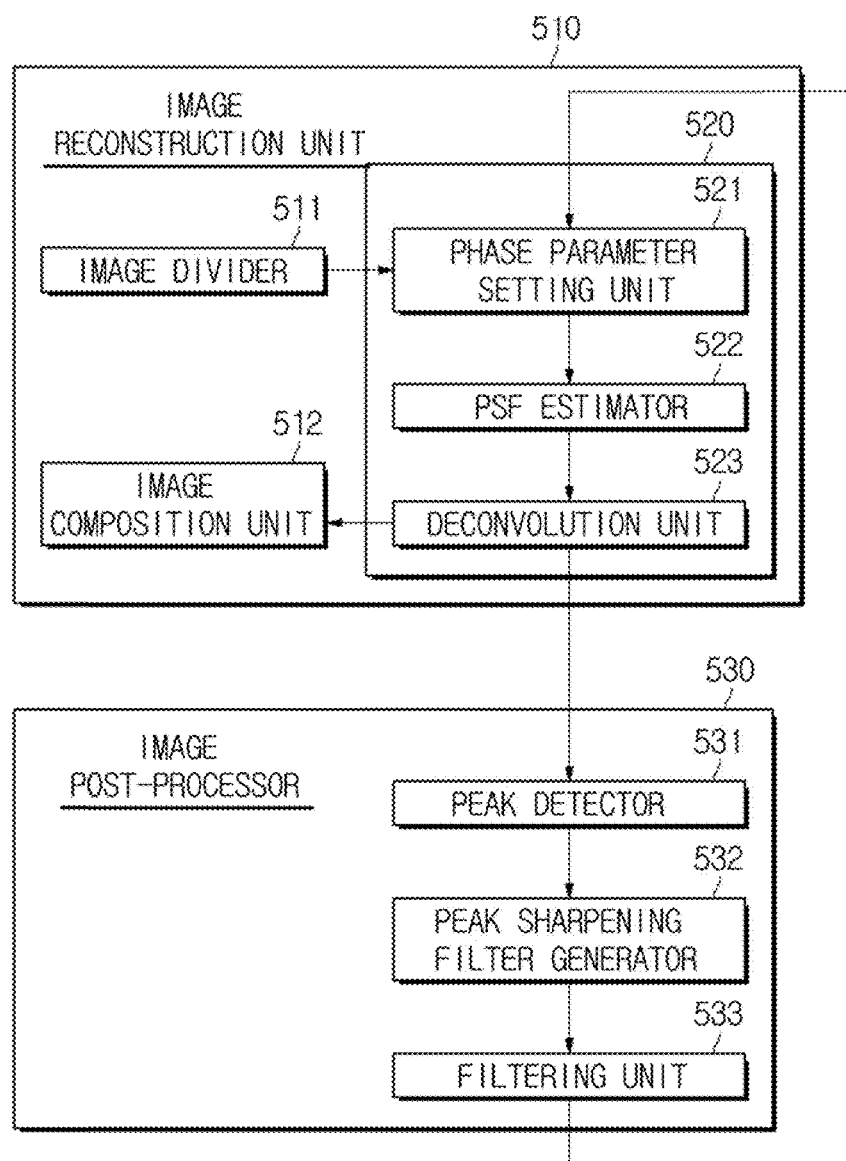
FIG. 7 is a block diagram of an image generator, according to an exemplary embodiment.

Configurations and relationships thereof between the image reconstruction unit 510 and the image post-processor 530 will be described in more detail with reference to FIG. 7. FIG. 7 is a block diagram of an image generator, according to an exemplary embodiment.

Referring to FIG. 7, in the image generator 500, the image reconstruction unit 510 may include an image divider 511, an image composition unit (also referred to herein as an "image composer") 512, a phase parameter setting unit (also referred to herein as a "phase parameter setter") 521, a PSF estimator 522, and a deconvolution unit (also referred to herein as a "deconvolver") 523, and the image post-processor 530 may include a peak detector 531, a peak sharpening filter generator 532, and a filtering unit (also referred to herein as a "filter") 533.

The image divider 511 may divide an ultrasonic image corresponding to the input signal I into at least one area. Dividing the ultrasonic image may be performed based on a result of analyzing the ultrasonic image, and in this regard, at least one situational factor may be used as a basis for division. The situational factor may include any one or more of a distance between the probe 200 and the target part (i.e., a depth to the target part), a speed of the ultrasound signal (sound velocity), etc.

For example, the image divider 511 may analyze the speed of the ultrasound signal that appears in the ultrasonic image, and divide the ultrasonic image into at least one area based on the speed of the ultrasound signal. The image divider 511 may also analyze the depth to the target part that appears in the ultrasonic image, and divide the ultrasonic image into at least one area based on the depth to the target part. It is also possible to divide the ultrasonic image by analyzing the speed of the ultrasound signal and the depth to a target part that appear in the ultrasonic image, in conjunction with one another.

Inclusion of the speed of the ultrasound signal and the depth to the target part in the basis for division may occur because a PSF generated based on the ultrasonic image is most affected by the speed of the ultrasound signal or the depth to a target part. This will be examined in more detail with reference to FIGS. 8, 9, 10A, 10B, and 10C.

Figure 8:
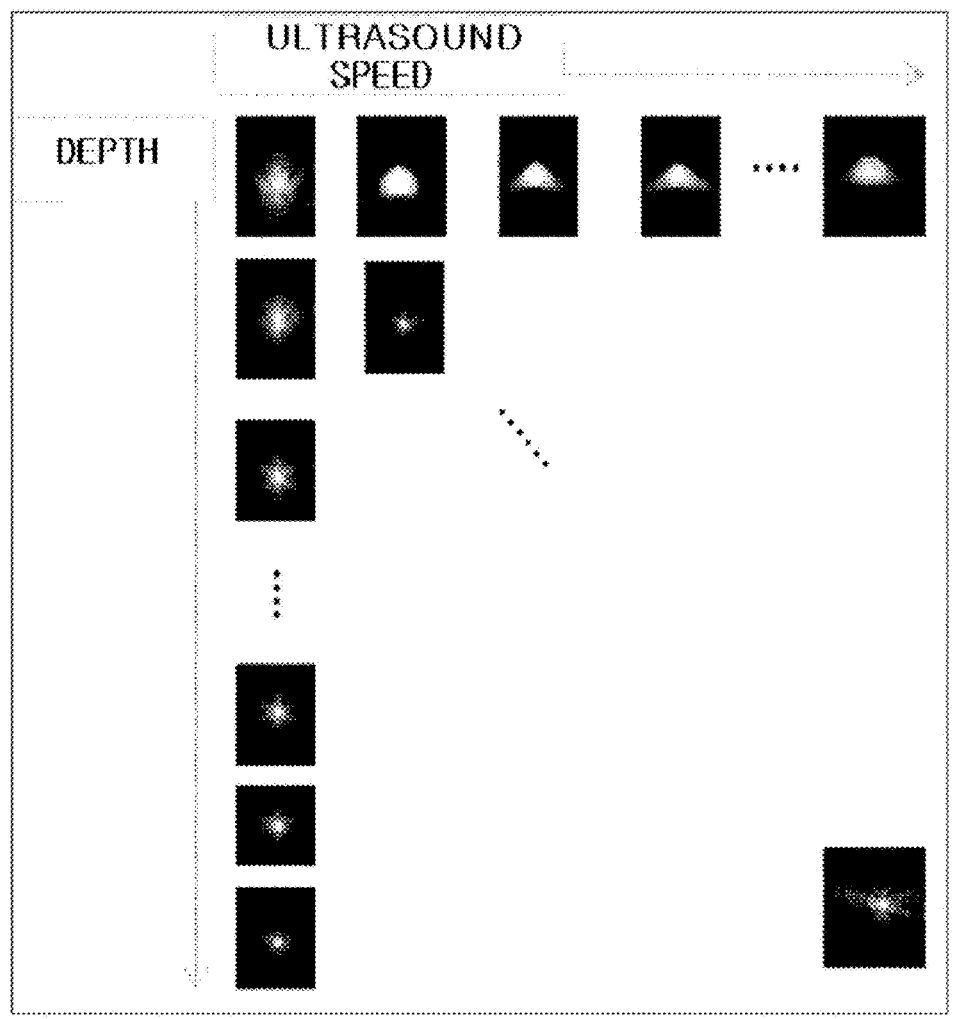
FIG. 8 illustrates a two dimensional (2D) point estimation function.

FIG. 8 illustrates a two dimensional (2D) point estimation function.

Referring to FIG. 8, a set of 2D PSFs obtained based on the situational factors of the ultrasound speed and the depth to a target part are illustrated. As can be seen from FIG. 8, even with the same method for obtaining 2D PSFs, the shape or extent of spread of the 2D PSFs varies based on whether the ultrasound speed is fast or slow or whether the depth of a target part is deep or shallow.

Figure 9A:
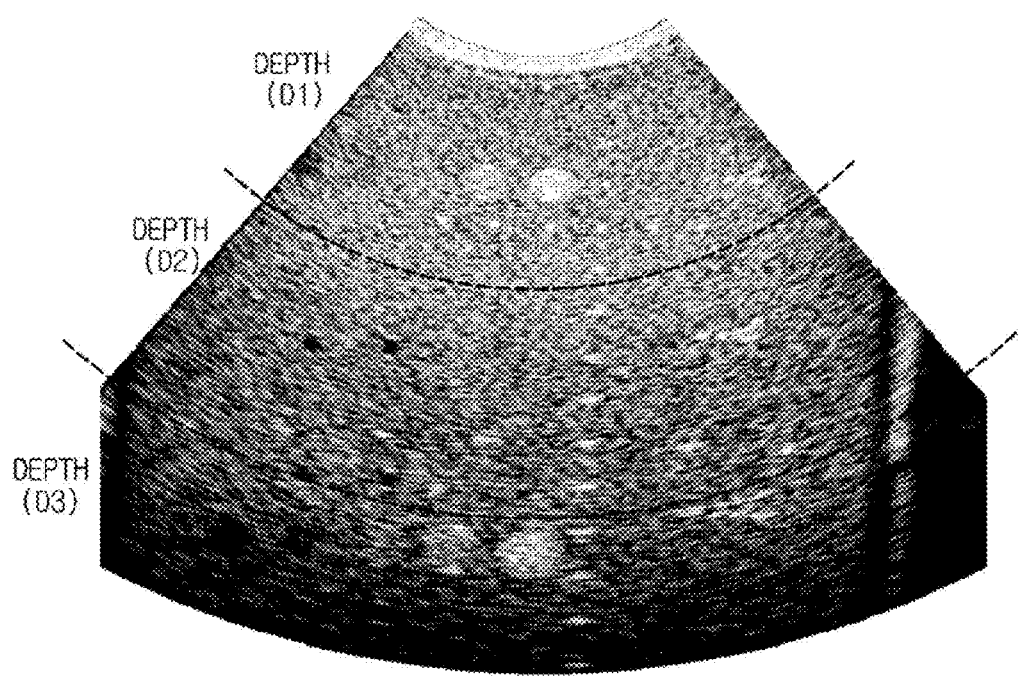
FIG. 9A illustrates a division of an ultrasonic image by depth.
Figure 9B:
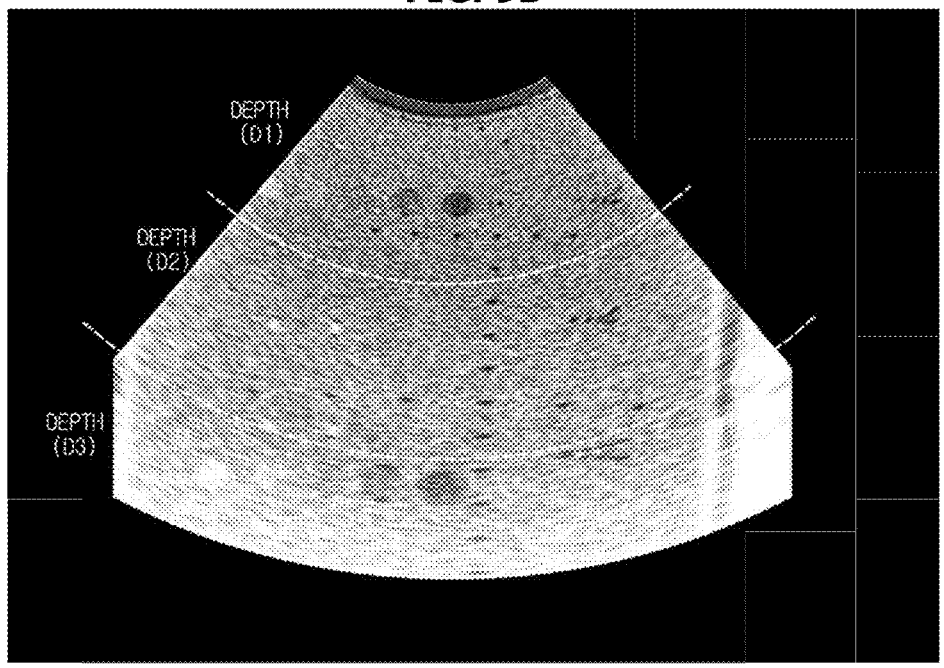
FIG. 9B illustrates color inversion image of FIG. 9A.

FIG. 9A illustrates division of an ultrasonic image by depth. FIG. 9B illustrates color inversion image of FIG. 9A.

Referring to FIG. 9A and FIG. 9B, the image divider 511 may divide an ultrasonic image into three areas by depth to a target part. Specifically, the image divider 511 may divide the ultrasonic image into areas D1 for depth 1, D2 for depth 2, and D3 for depth 3. As the depth grows from depth 1 to depth 3, the depth to the target part gets deeper.

Figure 10B:
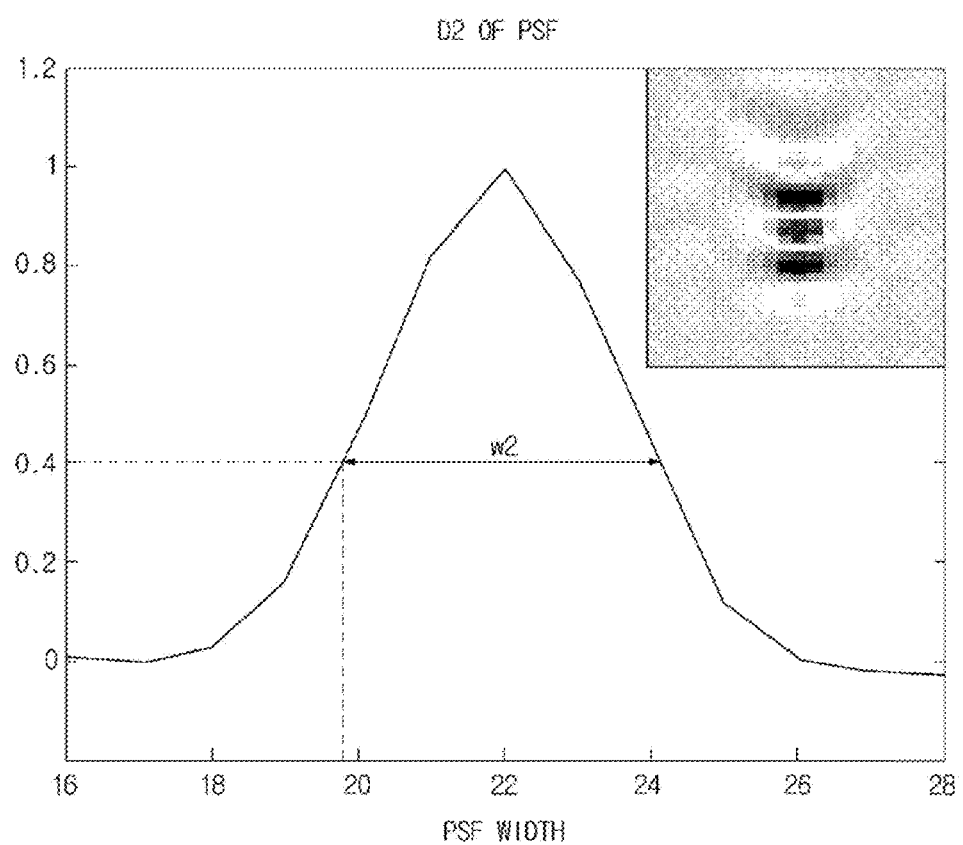
Figure 10C:
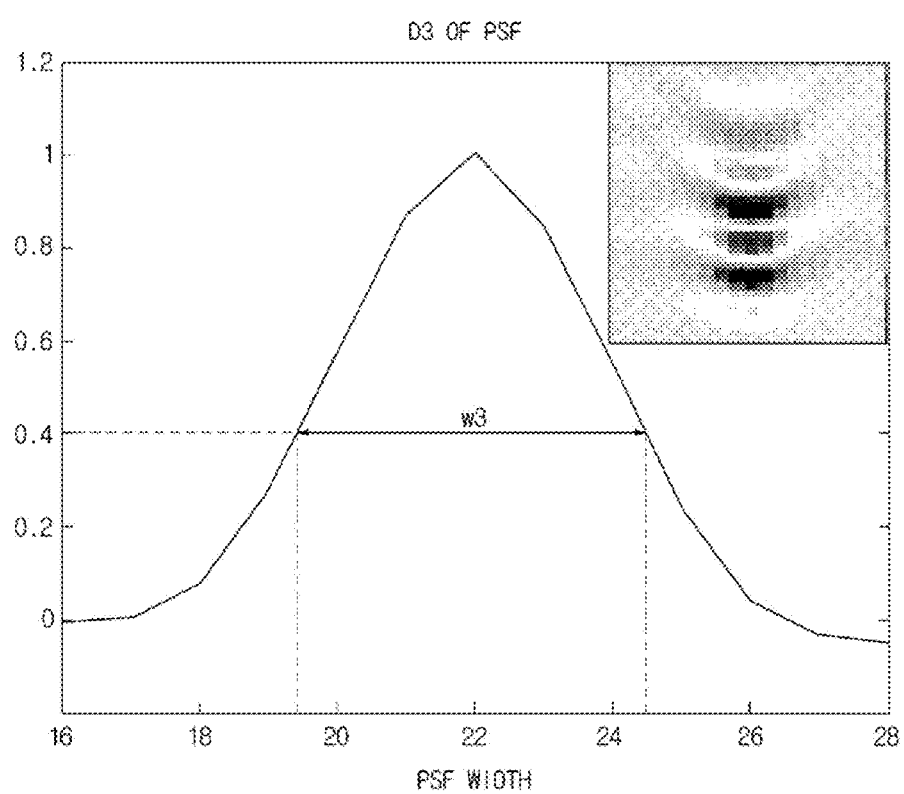

FIGS. 10A, 10B, and 10C illustrate PSFs which respectively correspond to the divided areas of FIG. 9A. More specifically, FIG. 10A illustrates a graph of a PSF corresponding to the area D1 in the ultrasonic image of FIG. 9A; FIG. 10B illustrates a graph of a PSF corresponding to the area D2 in the ultrasonic image of FIG. 9A; and FIG. 10C illustrates a graph of a PSF corresponding to the area D3 in the ultrasonic image of FIG. 9A. In FIGS. 10A, 10B, and 10C, graphs of 2D PSFs are shown on the upper right, and graphs of one dimensional (1D) PSFs (cross-sectional graphs in the side direction of the 2D PSFs) are shown on the lower left.

As described above, it can be seen from FIGS. 10A, 10B, and 10C that the shape or extent of spread of the 2D PSFs varies based on whether the target part is deep (like area D3) or shallow (like area D1).

Specifically, the extent of spread in all directions of the 2D PSF for the area D2 is smaller than that of the 2D PSF for the area D3, but greater than that of the 2D PSF for the area D1.

Similarly, the extent w2 of spread in the left and right directions of the 1D PSF for the area D2 is smaller than the extent of spread w3 in the left and right directions of the 1D PSF for the area D3, but greater than the extent of spread w1 in the left and right directions of the 2D PSF for the area D1.

As such, since the PSF generated based on the ultrasonic image is largely affected by the depth to a target part, the image divider 511 may divide the ultrasonic image into e.g., three areas by depth to the target part, as shown in FIG. 9A.

What is shown in FIG. 9A is merely by way of example, and there may be a greater or a fewer number of divided areas. Of course, it is possible for the image divider 511 to divide the ultrasonic image based on any other situational factor.

Some divided areas included in the ultrasonic image may have the same size or different sizes. In case of dividing multiple ultrasonic images, the image divider 511 may apply the same method to divide each of the multiple ultrasonic images. In particular, the multiple ultrasonic images may be divided into the same number of areas in the same size.

However, for convenience of explanation, description will be made based on a single ultrasonic image being divided by depth into three areas D1, D2, and D3 in the same size.

The phase parameter setting unit 521 may set a phase parameter to be used by the PSF estimator 522. The phase parameter may be defined as parameterized phase information which is required for estimation of a PSF.

The phase parameter setting unit 521 may set one or more initial phase parameters for the areas.

For example, initial parameter p1,1 may be set for the area D1; p2,1 for the area D2; and p3,1 for the area D3.

The phase parameter setting unit 521 may update the phase parameter by using an image filtered by the filtering unit 533. A number of updating times may be input from the user or may be set in advance, and is assumed herein to be nine times.

In this regard, for the area D1, it may be defined that the initial phase parameter p1,1 is updated to a second phase parameter p1,2, and the second phase parameter p1,2 is updated to a third phase parameter p1,3. In this manner, up to tenth for the area D1, i.e., a tenth phase parameter p1,10 may be defined as a result of nine times of updating.

Likewise, $j^{th}$ phase parameter p2,j for the area D2 and $j^{th}$ phase parameter p3,j for the area D3 may be defined, where j=1, 2, 3, ..., 10.

A method for using the filtered image to update the phase parameter in the phase parameter setting unit 521 will be described below in conjunction with the description of the filtering unit 533.

The PSF estimator 522 may estimate at least one PSF for an ultrasonic image. The at least one PSF may include either 1D PSF or 2D PSF. It is also possible that both of 1D and 2D PSFs may be estimated. In some exemplary embodiments, three dimensional (3D) or four or greater dimensional PSFs may be estimated.

As an example of estimating a 1D PSF, an Autoregressive Moving Average (ARMA) method may be used. Such estimation of 1D PSF may be advantageously performed in a short period of time.

As an example of estimating a 2D PSF, a Cepstrum method may be used. The Cepstrum method may be advantageously used in order to transform an ultrasonic image from the spatial domain to the Cepstrum domain and then estimate the 2D PSF in the Cepstrum domain.

The Cepstrum method is classified into a method of estimating the 2D PSF in consideration of only size information of the ultrasonic image and a method of estimating the 2D PSF in consideration of both the size information and phase information of the ultrasonic image. The estimation method in consideration of the size information only may accelerate the estimation speed, while the estimation method in consideration of both the size and phase information may increase accuracy of estimation.

The PSF estimator 522 may estimate a 1D or greater dimensional PSF by using the aforementioned method, but for convenience of explanation it is assumed herein that the PSF estimator 522 estimates a 2D PSF using the Cepstrum method.

The PSF estimator 522 may estimate a PSF using the size and phase information of an ultrasound image. This is illustrated more specifically with reference to the following equations 2 to 6.

$$\hat{g}_R(m,n) = DFT^{-1}[\log|DFT\{g_R(m,n)\}|] \quad (2)$$

where $g_R$ indicates an ultrasonic image, DFT indicates Discrete Fourier Transformation, and log indicates a logarithm function.

Specifically, in equation 2, $\hat{g}_R$ is obtained by eliminating noise w from the ultrasonic image $g_R$ of equation 1, performing DFT, transforming into a linear form using the logarithm function, and performing Inverse DFT (IDFT) for transformation into the Cepstrum domain.

$$\hat{h}(m, n) = \hat{g}_R(m, n)\{p \cdot a(n) + (1 - p)\}, \quad (3)$$

$$a(n) = \begin{cases} 0 & (n < 0) \\ 1 & (n = 0) \\ 2 & (n < 0) \end{cases}$$

In equation 3, a PSF in the Cepstrum area, $\hat{h}$, is obtained by applying a phase parameter p and a window a to the ultrasonic image $\hat{g}_R$ in the Cepstrum domain.

$$h(m,n) = DFT^{-1}[\exp\{DFT\{\hat{h}(m,n)\}\}] \quad (4)$$

In equation 4, the PSF $\hat{h}$ in the Cepstrum domain obtained in equation 3 is transformed back to a PSF h in the space domain. exp refers to an exponential function.

The PSF estimator 522 may estimate the PSF h through the procedure similarly as in equations 2 to 4. However, the aforementioned equations are only examples of estimating a PSF, and other equations or other methods may also be possible for estimation of the PSF.

The PSF estimator 522 estimates PSFs in accordance with the number of phase parameters. Thus, an estimated PSF corresponding to the phase parameter pi,j, where i=1, 2, 3, and j=1, 2, 3, ..., 10, may be defined as hi,j. For example, for the area D1, an estimated PSF corresponding to p1,1 set as the initial phase parameter may be defined as h1,1; an estimated PSF corresponding to the second phase parameter p1,2 may be defined as h1,2; and an estimated PSF corresponding to the final phase parameter p1,10 may be defined as h1,10.

The deconvolution unit 523 may generate a reconstructed image for each area of the ultrasonic image by performing a deconvolution of the PSF estimated by the PSF estimator 522 and the corresponding area.

As an example of deconvolution, equation 5 may be used.

$$R(m, n) = DFT^{-1}\left[\frac{DFT\{g_R(m, n)\}}{DFT\{h(m, n) + e_1\}}\right] \quad (5)$$

$g_R$ indicates an ultrasonic image of equation 1, h indicates a PSF of equation 4, and e1 is a constant.

The deconvolution unit 523 uses equation 5 to perform deconvolution of the ultrasonic image $g_R$ and the PSF h, thus generating a reconstructed image R.

Specifically, since h1,1 was estimated first for the area D1 of the ultrasonic image, the deconvolution unit 523 generates a first reconstructed image for the area D1 by performing a deconvolution of the area D1 and h1,1. Further, since h1,2 was estimated second for the area D1, the deconvolution unit 523 generates a second reconstructed image for the area D1 by performing a deconvolution of the area D1 and h1,2. The first and second reconstructed images for the area D1 may be defined as R1,1 and R1,2, respectively.

As described above, the deconvolution unit 523 generates the jth reconstructed image R1,j for the area D1 by deconvolution of the area D1 and h1,j, where j=1, 2, 3, . . . , 10.

Likewise, the deconvolution unit 523 generates the $j^{th}$ reconstructed image R2,j for the area D2 and the jth reconstructed image R3,j for the area D3.

In the order the reconstructed images are generated, a set of first reconstructed images R1,1, R2,1, and R3,1 for the areas are collectively referred to as the first reconstructed image; a set of second reconstructed images R1,2, R2,2, and R3,2 for the areas are collectively referred to as the second reconstructed image, and, in the same way, jth reconstructed images for the areas are collectively referred to as the jth reconstructed image, where j=1, 2, 3, . . . , 10.

The first to ninth reconstructed images generated by the deconvolution unit 523 may be output in the generation sequence to the peak detector 531 of the image post-processor 530 for filtering. The tenth reconstructed image generated last may be output to the image composition unit 512 for image composition.

The image composition unit 512 may compose the tenth reconstructed images generated by the deconvolution unit 523.

Specifically, the image composition unit 512 generates final reconstructed image for the entire areas of the ultrasonic image by composing the tenth (or the last) reconstructed image R1,10 for the area D1 of the ultrasonic image, the tenth reconstructed image R2,10 for the area D2, and the tenth reconstructed image R3,10 for the area D3 to fit the respective areas.

The final reconstructed image generated by the image composition unit 512 is output to the display unit 720.

Referring again to FIG. 7, the peak detector 531 of the image post-processor 530 may detect a peak point from the reconstructed image for each area input from the deconvolution unit 523.

Only with the first to ninth reconstructed images input from the deconvolution unit 523, the peak detector 531 does not detect the peak point of the last tenth reconstructed image for each area.

The peak point may include any one or more of a 2D peak point in a 2D image or may be an 1D peak point in an 1D image, a cross-sectional image in a side direction L and/or an elevation direction E.

Once the peak point is detected by the peak detector 531, the peak sharpening filter generator 532 may generate a peak sharpening filter in order to stress, i.e., emphasize, a peak point in the reconstructed image for each area.

Specifically, the sharpening filter generator 532 generates peak sharpening filters F1,1, F2,1, and F3,1 for the first, second, and third reconstructed images R1,1, R2,1, and R3,1, respectively, and generates peak sharpening filters F1,2, F2,2, and F3,2 for the second reconstructed images R1,2, R2,2, and R3,2, respectively. Likewise, the peak sharpening filter generator 532 generates peak sharpening filters F1,j, F2,j, and F3,j for the jth reconstructed images R1,j, R2,j, and R3,j, where j=1,2,3, . . . , 10.

The filtering unit 533 may filter the reconstructed image for each area by using the corresponding peak sharpening filter.

For example, the filtering unit 533 filters the first reconstructed images R1,1, R2,1, and R3,1 input first, by means of the corresponding peak sharpening filters F1,1, F2,1, and F3,1. Specifically, the filter F1,1 filters the reconstructed image R1,1, the filter F2,1 filters the reconstructed image R2,1, and the filter F3,1 filters the reconstructed image R3,1. Next, the filtering unit 533 filters the second reconstructed images R1,2, R2,2, and R3,2 input second, by means of the corresponding peak sharpening filters F1,2, F2,2, and F3,3. As such, the filtering unit 533 completes filtering of up to the ninth reconstructed images R1,9, R2,9, and R3,9.

Operations of the peak detector 531 detecting the peak point, the peak sharpening filter generator 531 generating the filter, and the filtering unit 533 performing filtering will be described in more detail in connection with FIGS. 11 and 12.

Figure 11:
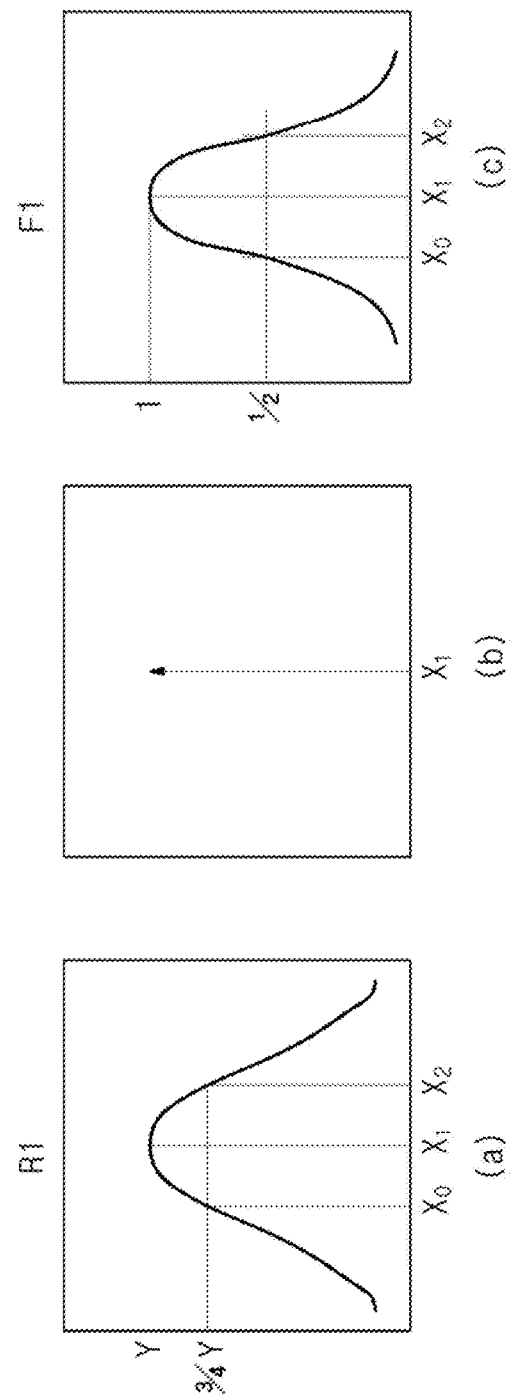
FIG. 11 illustrates how to generate a peak sharpening filter.
Figure 12:
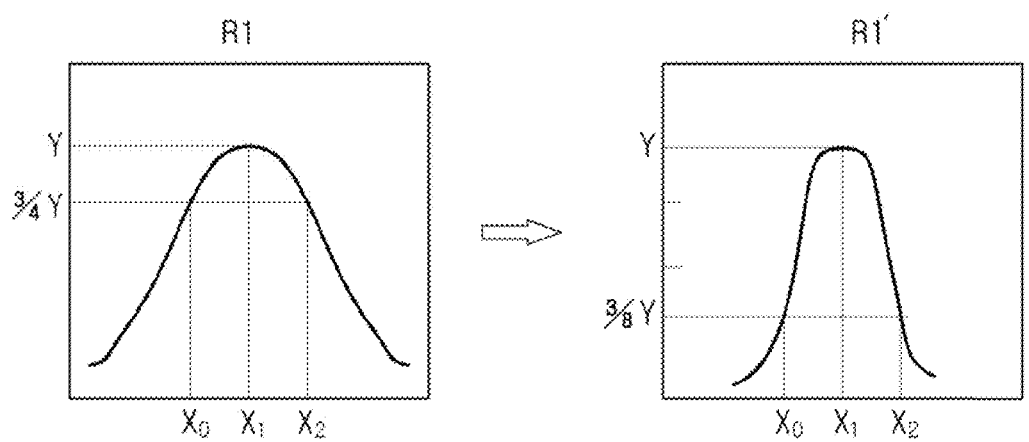
FIG. 12 illustrates a comparison of an image before filtering with an image after filtering.

FIG. 11 illustrates how to generate a peak sharpening filter.

Specifically, drawing (a) of FIG. 11 illustrates coordinates and image values of an image $I_0$, drawing (b) of FIG. 11 illustrates a detected peak point of the image $I_0$, and drawing (c) of FIG. 11 illustrates a peak sharpening filter $F_1$ generated based on the detected peak point. The image $I_0$ may be a reconstructed image that is a result of a deconvolution operation. The horizontal axes of drawings (a), (b), and (c) of FIG. 11 each refer to the x-axis in the spatial plane, the vertical axis of drawing (a) of FIG. 11 refers to image values, and the vertical axis of drawing (c) of FIG. 11 refers to filter values.

As shown in drawing (a) of FIG. 11, for the image $I_0$, an image value of $X_1$ is Y, and as a value on the x-axis gets farther from $X_1$, a corresponding image value is reduced, and thus an image value at X0 or X2 becomes ¾Y.

When a point having a higher image value than others do is defined as a peak point, the peak detector 531 detects X1 as a peak point, as shown in drawing (b) of FIG. 11, and generates an impulse signal which corresponds to the peak point.

With the impulse signal for the peak point, the peak sharpening filter generator 532 applies a low pass filter to the impulse signal to convert it into a Gaussian shape. In particular, a filter is generated such that the filter value is reduced as a value on the x-axis gets farther from the peak point. Thus, the peak sharpening filter generator 532 may generate a filter having a filter value '1' at the peak point $X_1$ and a filter value '½' at $X_0$ or $X_2$, which is some distance apart from the peak point $X_1$, as shown in drawing (c) of FIG. 11.

Once the peak sharpening filter generator 532 generates a peak sharpening filter in a Gaussian shape, as described above, the filtering unit 533 performs filtering for obtaining an inner product of the reconstructed image that underwent deconvolution and the corresponding peak sharpening filter. Accordingly, an image resulting from the reconstructed image with an emphasized peak point, or to be more exact, with a sharpened peak point, may be generated. FIG. 12 illustrates a comparison of images before and after filtering. On the left side of FIG. 12 is an image before filtering, similarly as shown in drawing (a) of FIG. 11, and on the right side of FIG. 12 is an image after filtering with the filter, similarly as shown in drawing (c) of FIG. 11.

The peak point $X_1$ in the image after filtering has an image value Y, which is the same as in the image before filtering. However, the extent to which the image value decreases as a value on the x-axis gets far from $X_1$ is greater than that of the image before filtering. For example, $X_0$ or $X_2$ having an image value ¾Y in the image before filtering has an image value ⅜Y in the image after filtering.

In particular, the image after filtering has a sharpened peak point, as compared to the image before filtering.

As described above, the filtering unit 533 may perform filtering on the first to ninth reconstructed images input from the deconvolution unit 523 in the order of reception.

Further, the filtering unit 533 may output filtered images back to the phase parameter setting unit 521 of the image reconstruction unit 510 in the order of reception. For example, the filtering unit 533 may output an image resulting from filtering of the first reconstructed image to the phase parameter setting unit 521 in order to update phase parameters p1,1, p2,1, and p3,1, and output an image resulting from filtering of the second reconstructed image to the phase parameter setting unit 521 in order to update phase parameters p1,2, p2,2, and p3,2.

An example of a method of using a filtered image to update phase parameters in the phase parameter setting unit 521 may be expressed as in equations 6 and 7.

The phase parameter setting unit 521 may first obtain a PSF, hc, compensated as expressed in the following equation 6.

$$hc(m, n) = DFT^{-1}\left[\frac{DFT\{g_R(m, n)\}}{DFT\{R'(m, n) + e_2\}}\right] \quad (6)$$

where $g_R$ indicates an ultrasonic image of equation 1, R' indicates an image resulting from filtering of the reconstructed image R of equation 5, i.e., an image with an emphasized peak point, and e2 is a constant.

The phase parameter setting unit 521 may obtain a phase parameter p which is updated by using the following equation 7.

$$DFT\{hc(m,n)\} = \exp\{DFT\{\hat{h}(m,n)\}\} \quad (7)$$

where $\hat{h}$ indicates a PSF in the Cepstrum domain of equation 1, and hc indicates a compensated PSF of equation 6.

The phase parameter setting unit 521 updates the phase parameter as many times as input by the user or as determined in advance, and the phase parameter converges on a predetermined value as it continues to be updated.

In this aspect, the ultrasonic image input to the image divider 511 is reconstructed per divided area while being processed by the phase parameter setting unit 521, the PSF estimator 522, and the deconvolution unit 523 in sequence. In particular, the first reconstructed image is generated. The first reconstructed image is filtered to have an emphasized peak point while being processed by the peak detector 531, the peak sharpening generator 532, and the filtering unit 533 in sequence. The filtered image is input back to the phase parameter setting unit 521 and is processed by the PSF estimator 522 and the deconvolution unit 523, thereby being newly reconstructed per divided area. Again, the second reconstructed image is generated. Once up to tenth reconstructed image is generated by repetition of the procedure, the image composition unit 512 generates a final reconstructed image for the entire areas via image composition.

FIGS. 13, 14, 15, and 16 illustrate procedures and results of generating the final reconstructed image.

FIG. 13 is a graph of a phase parameter as a function of repetition times.

The phase parameter may include a phase parameter in any of the divided areas (e.g., the area D1).

Referring to FIG. 13, if the phase parameter setting unit 521 sets the initial phase parameter to −0.2, the phase parameter is gradually reduced to converge near to −1.2 as the number of repetition times or updating times of the phase parameter increases.

Figure 15B:
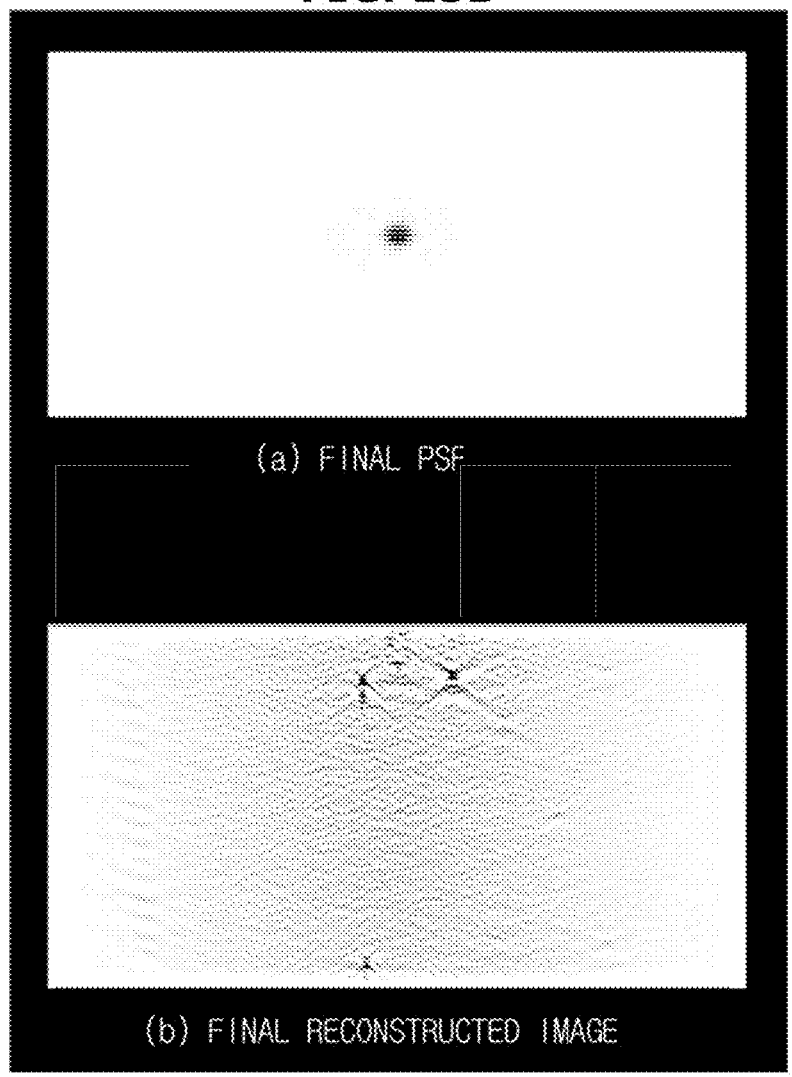
FIG. 15B illustrates color inversion image of FIG. 15A.

FIG. 14A illustrates an initially estimated PSF, a first reconstructed image, and an image obtained by filtering the first reconstructed image. FIG. 14B illustrates color inversion image of FIG. 14A. FIG. 15A illustrates a finally estimated PSF and a finally reconstructed image. FIG. 15B illustrates color inversion image of FIG. 15A.

The PSF shown in illustration (a) of FIG. 14A is an initial PSF estimated using an initially set phase parameter and is represented as a first PSF. The reconstructed image shown in illustration (b) of FIG. 14A is a first reconstructed image reconstructed from an ultrasonic image by using the first PSF. The image shown in illustration (c) of FIG. 14A is a first filtered image obtained by stressing the peak point in the first reconstructed image, i.e., an image after a peak sharpening filter is applied, and is represented as a first filtered image.

Illustration (a) of FIG. 15A shows a final PSF estimated using a finally updated phase parameter. The image shown in illustration (b) of FIG. 15A is a final reconstructed image reconstructed from an ultrasonic image by using the final PSF.

Compared with the first reconstructed image of illustration (b) of FIG. 14A, edges are emphasized while the other parts are smoothed out in the final reconstructed image of illustration (b) of FIG. 15A. In particular, it can be seen that the final reconstructed image has more improved resolution than the first reconstructed image does.

Figure 16A:
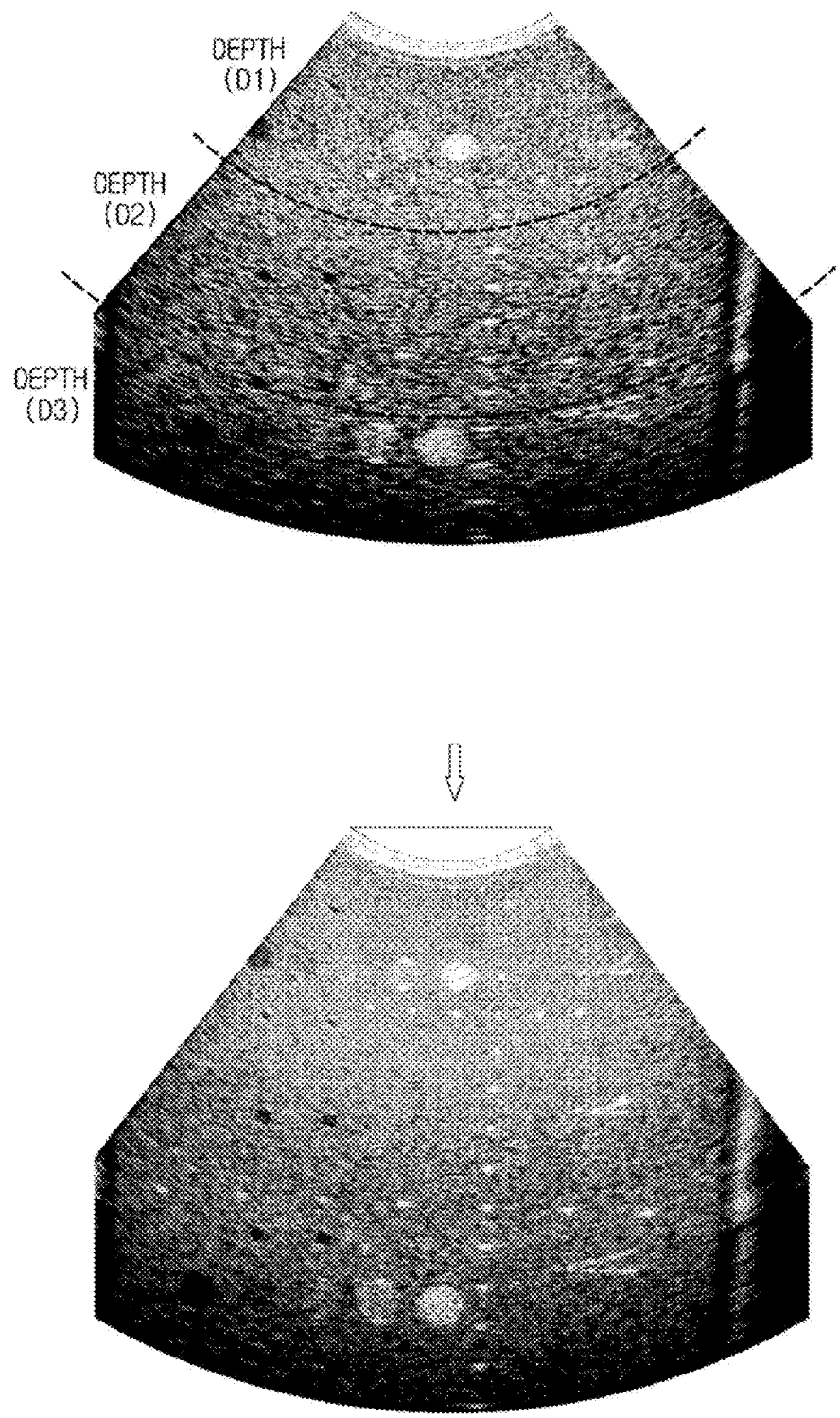
FIG. 16A illustrates a finally reconstructed image for the ultrasonic image shown in FIG. 9A.
Figure 16B:
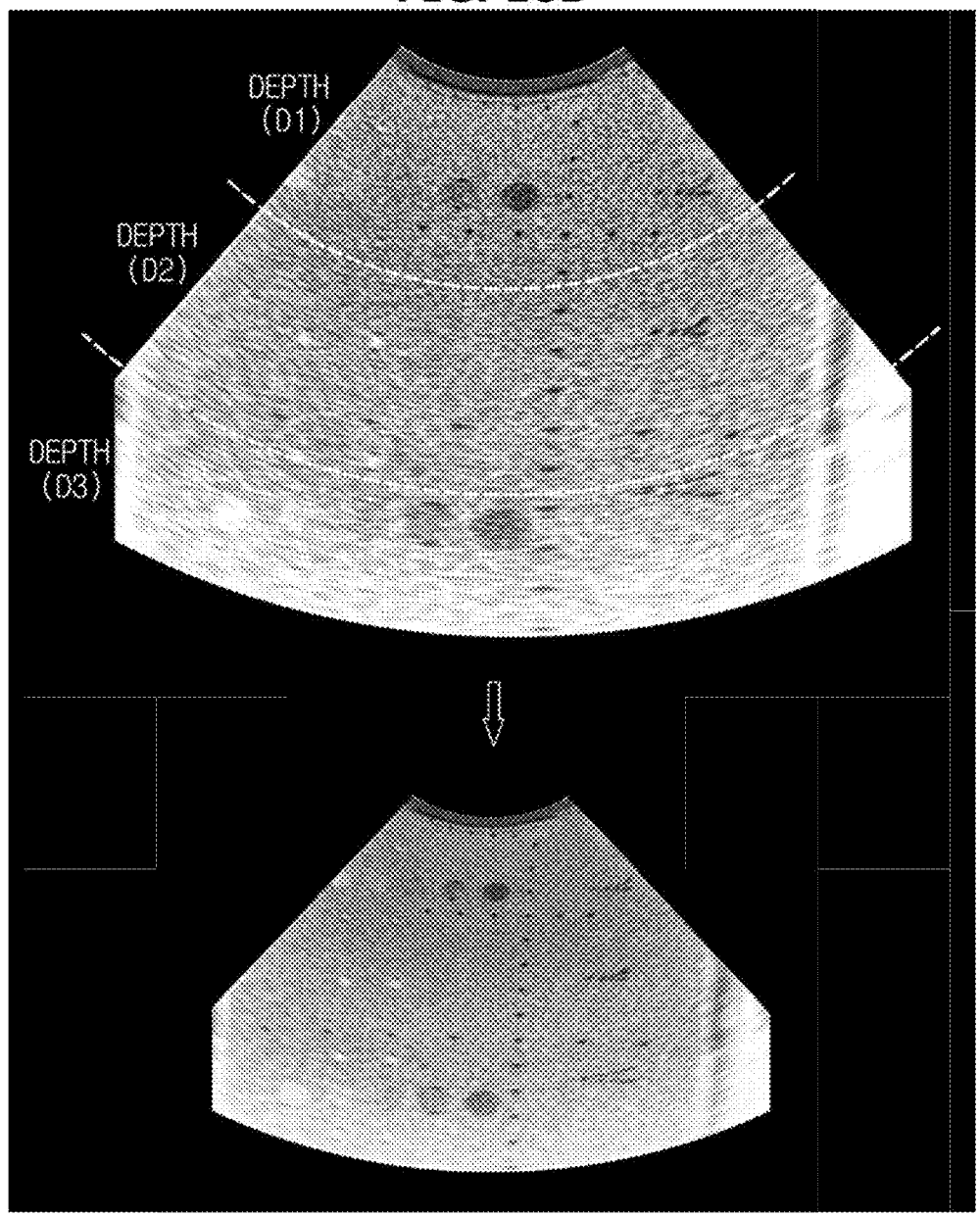
FIG. 16B illustrates color inversion image of FIG. 16A.

FIG. 16A illustrates a finally reconstructed image for the ultrasonic image shown in FIG. 9A. FIG. 16B illustrates color inversion image of FIG. 16A. The upper image is the ultrasonic image and the lower image is the finally reconstructed image.

As the depth grows deeper in the ultrasonic image from D1 to D2 to D3, the ultrasonic image has a shape gradually spreading in all directions. Conversely, it can be seen from the final reconstructed image that the extent to which the image spreads in all directions as the depth grows deeper is clearly reduced.

Exemplary embodiments of configurations and functions of an ultrasound imaging apparatus have thus far been described, and a method for controlling the ultrasound imaging apparatus will now be described with reference to a given flowchart.

Figure 17:
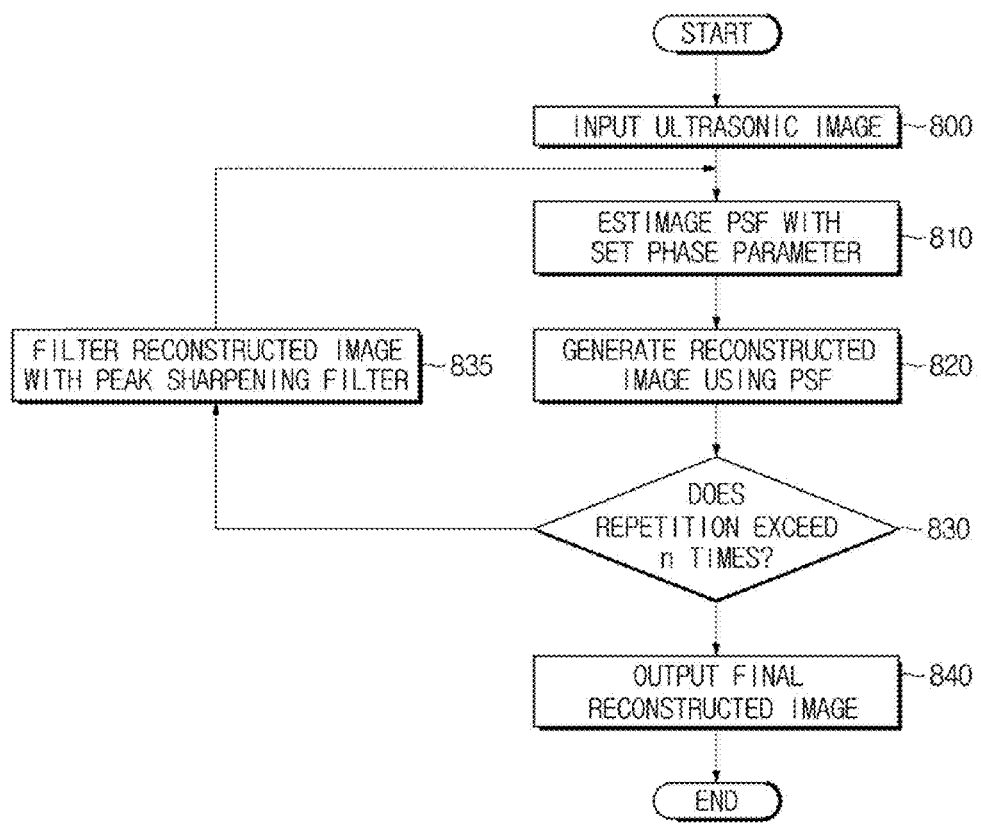
FIG. 17 is a flowchart illustrating a method for controlling an ultrasound imaging apparatus, according to an exemplary embodiment.

FIG. 17 is a flowchart illustrating a method for controlling an ultrasound imaging apparatus, according to an exemplary embodiment.

Referring to FIG. 7, an ultrasonic image is input in operation 800.

The ultrasonic image is an image which corresponds to an input signal I, as described above. The ultrasonic image is an image modified due to technical or mechanical properties of the probe 200 or beamformer 350 and to which noise is further added. In this aspect, the ultrasonic image has a degraded image quality.

A phase parameter is set based on the input ultrasonic image and a PSF is estimated by using the phase parameter, in operation 810.

In performing an estimation of a PSF, a Cepstrum method may be applied, by which an ultrasonic image is transformed from the spatial domain to the Cepstrum domain and then a 2D PSF is estimated in the Cepstrum domain.

A reconstructed image is generated by using the estimated PSF, in operation 820.

In particular, a reconstructed image for the ultrasonic image is generated by performing a deconvolution of the ultrasonic image with the PSF.

It is determined whether the number of repetitions of generating a reconstructed image exceeds n times, in operation 830. The repetition times n may be input by the user or set in advance.

If it is determined that the number of repetitions exceeds n times, the reconstructed image is filtered by using a peak sharpening filter, in operation 835.

Then, the procedure goes back to operation 810. At this stage, the phase parameter is updated by using the filtered image, and an updated PSF is estimated by using the updated phase parameter. An updated reconstructed image is generated by using the updated estimated PSF, in operation 820.

If it is determined that the number of repetitions exceeds n times, in operation 830, a final reconstructed image is output to a display unit for the user to see a resulting image of an inside of an object, in operation 840.

Compared with the ultrasonic image, the extent to which the final reconstructed image spreads as the depth grows deeper is reduced and the resolution is improved, which helps the user with ultrasonic diagnosis.

According to the ultrasound imaging apparatus and method for controlling the same, a filter to emphasize a peak point may facilitate an accurate setting of a phase parameter to be used in estimation of a PSF.

Accordingly, an almost ideal PSF may be estimated, image reconstruction is performed using the estimated PSF, and thus a high resolution image may be obtained.

Several exemplary embodiments have thus been described with respect to an ultrasound imaging apparatus and method for controlling the same, but it will be understood that various modifications can be made without departing the scope of the present disclosure. Thus, it will be apparent to those of ordinary skill in the art that the disclosure is not limited to the exemplary embodiments described, but can encompass not only the appended claims but the equivalents.

What is claimed is:

1. An ultrasound imaging apparatus comprising:
an ultrasonic probe configured to transmit an ultrasound signal toward an object, receive an echo ultrasound signal which is reflected from the object, and transform the received echo ultrasound signal to an electric signal;
a beamformer configured to beamform and output the electric signal;
an image generator circuitry configured to estimate a Point Spread Function (PSF) based on an ultrasonic image which corresponds to the output electric signal, and configured to generate a reconstructed image by using the estimated PSF,
wherein the image generator circuitry is further configured to generate an impulse signal for a peak point of the reconstructed image, to generate a peak sharpening filter in a Gaussian form by filtering the impulse signal using a low pass filter, and to perform filtering on the reconstructed image by using the peak sharpening filter.

2. The ultrasound imaging apparatus of claim 1, wherein the image generator circuitry is further configured to detect the peak point from the reconstructed image, and to generate the peak sharpening filter based on the detected peak point.

3. The ultrasound imaging apparatus of claim 1, wherein the image generator circuitry is further configured to:
set a parameter based on the ultrasonic image;
generate the estimated PSF by using the parameter; and
generate the reconstructed image by using the generated estimated PSF based on the ultrasonic image.

4. The ultrasound imaging apparatus of claim 3, wherein the image generator circuitry is further configured to update the parameter by using the filtered image.

5. The ultrasound imaging apparatus of claim 4, wherein the image generator circuitry is further configured to estimate an updated PSF by using the updated parameter.

6. The ultrasound imaging apparatus of claim 5, wherein the image generator circuitry is further configured to generate an updated reconstructed image by using the updated PSF to the ultrasonic image.

7. The ultrasound imaging apparatus of claim 3, wherein the image generator circuitry is further configured to transform the ultrasonic image into a Cepstrum domain, and to estimate the PSF by estimating a two dimensional (2D) PSF in the Cepstrum domain.

8. The ultrasound imaging apparatus of claim 1, wherein the image generator circuitry is further configured to generate the reconstructed image by performing a deconvolution of the ultrasonic image and the PSF.

9. The ultrasound imaging apparatus of claim 1, wherein the image generator circuitry is further configured to divide the ultrasonic image into a plurality of areas.

10. The ultrasound imaging apparatus of claim 9, wherein the image generator circuitry is further configured to generate at least one reconstructed image for each of the plurality of areas.

11. The ultrasound imaging apparatus of claim 10, wherein the image generator circuitry is further configured to perform filtering on each of the at least one reconstructed image.

12. The ultrasound imaging apparatus of claim 10, wherein the image generator circuitry is further configured to compose the at least one reconstructed image.

13. A method for controlling an ultrasound imaging apparatus, the method comprising:
transmitting an ultrasound signal toward an object, receiving an echo ultrasound signal reflected from the object, and transforming the received echo ultrasound signal to an electric signal;
beamforming and outputting the electric signal;
estimating a Point Spread Function (PSF) based on an ultrasonic image which corresponds to the output electric signal;
generating a reconstructed image by using the estimated PSF;
generating an impulse signal for a peak point of the reconstructed image, and generating a peak sharpening filter in a Gaussian form by filtering the impulse signal using a low pass filter; and
performing filtering on the reconstructed image by using the peak sharpening filter.

14. The method of claim 13, wherein the performing the filtering comprises:

detecting the peak point from the reconstructed image, and generating the peak sharpening filter based on the detected peak point.

15. The method of claim 13, wherein the generating the reconstructed image comprises:
setting a parameter based on the ultrasonic image;
generating the estimated PSF by using the parameter; and
generating the reconstructed image by using the generated estimated PSF for the ultrasonic image.

16. The method of claim 15, wherein the setting the parameter comprises:
updating the parameter by using the filtered image,
wherein the estimating the PSF comprises estimating an updated PSF by using the updated parameter, and
wherein the generating the reconstructed image comprises generating an updated reconstructed image by using the estimated updated PSF.

17. The method of claim 13, wherein the generating the reconstructed image comprises:
generating the reconstructed image by performing a deconvolution of the ultrasonic image and the PSF.

* * * * *